United States Patent
Jain et al.

(10) Patent No.: US 11,164,596 B2
(45) Date of Patent: Nov. 2, 2021

(54) SENSOR ASSISTED EVALUATION OF HEALTH AND REHABILITATION

(71) Applicant: Samsung Electronics Co., Ltd., Gyeonggi-Do (KR)

(72) Inventors: Jawahar Jain, Los Altos, CA (US); Cody Wortham, Mountain View, CA (US); James Young, Menlo Park, CA (US); Sajid Sadi, San Jose, CA (US); Pranav Mistry, Campbell, CA (US)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 1043 days.

(21) Appl. No.: 15/436,926

(22) Filed: Feb. 20, 2017

(65) Prior Publication Data
US 2017/0249438 A1    Aug. 31, 2017

Related U.S. Application Data

(60) Provisional application No. 62/300,028, filed on Feb. 25, 2016, provisional application No. 62/300,042, (Continued)

(51) Int. Cl.
*G10L 25/66* (2013.01)
*G10L 25/63* (2013.01)
(Continued)

(52) U.S. Cl.
CPC .............. *G10L 25/66* (2013.01); *G10L 25/63* (2013.01); *G16H 10/60* (2018.01); *G16H 20/30* (2018.01); *G16H 20/70* (2018.01); *G16H 50/30* (2018.01)

(58) Field of Classification Search
None
See application file for complete search history.

(56) References Cited

U.S. PATENT DOCUMENTS

| 5,144,949 A | 9/1992 | Olson |
| 5,410,472 A | 4/1995 | Anderson |

(Continued)

FOREIGN PATENT DOCUMENTS

| CN | 1080191 A | 8/2015 |
| CN | 104840191 A | 8/2015 |

(Continued)

OTHER PUBLICATIONS

Lu et al, A System for Limb-Volume Measurement using 3D Models from an Infrared Depth Sensor, 2013 IEEE Symposium on Computational Intelligence in Healthcare and e-health (CICARE) (Year: 2013).*

(Continued)

*Primary Examiner* — Gregory Lultschik
*Assistant Examiner* — William G Lultschik
(74) *Attorney, Agent, or Firm* — Cuenot, Forsythe & Kim, LLC

(57) ABSTRACT

A system for evaluating health-related quality of life (HRQOL) can include a sensor adapted to generate sensor data for a user, a memory adapted to store the sensor data, and a processor coupled to the sensor and the memory. The processor can be configured to initiate executable operations including determining a first biological marker for the user from the sensor data, wherein the first biological marker is indicative of a first dimension of HRQOL, performing speech analysis on user provided speech to determine a second biological marker indicative of a second dimension of HRQOL. The processor is further configured to initiate executable operations including comparing the first biological marker and the second biological marker with a baseline for the first biological marker and a baseline for the second biological marker, respectively, and outputting a result of the comparing.

18 Claims, 6 Drawing Sheets

Related U.S. Application Data filed on Feb. 25, 2016, provisional application No. 62/300,038, filed on Feb. 25, 2016.

(51) Int. Cl.
  *G16H 50/30* (2018.01)
  *G16H 20/70* (2018.01)
  *G16H 20/30* (2018.01)
  *G16H 10/60* (2018.01)

(56) References Cited

U.S. PATENT DOCUMENTS

| | | |
|---|---|---|
| 6,077,222 A | 6/2000 | Lloyd et al. |
| 6,190,324 B1 | 2/2001 | Kieval et al. |
| 6,472,988 B1 | 10/2002 | Feld et al. |
| 6,540,674 B2 | 4/2003 | Zadrozny et al. |
| 6,542,905 B1 | 4/2003 | Fogel |
| 6,904,311 B2 | 6/2005 | Freeberg |
| 7,142,920 B2 | 11/2006 | Scheiner et al. |
| 7,674,226 B2 | 3/2010 | Nadeau |
| 7,785,242 B2 | 8/2010 | Solomon |
| 7,853,455 B2 | 12/2010 | Brown |
| 7,869,877 B2 | 1/2011 | Kadhiresan |
| 7,877,277 B1 | 1/2011 | Petit et al. |
| 7,974,708 B2 | 7/2011 | Daum et al. |
| 7,993,268 B2 | 8/2011 | Nadeau |
| 8,118,712 B2 | 2/2012 | Thieberger et al. |
| 8,200,323 B2 | 6/2012 | Dibenedetto et al. |
| 8,303,500 B2 | 11/2012 | Raheman |
| 8,660,625 B2 | 2/2014 | Addison et al. |
| 8,719,214 B2 | 5/2014 | Stergiou et al. |
| 8,738,133 B2 | 5/2014 | Shuros et al. |
| 8,768,489 B2 | 7/2014 | Thieberger et al. |
| 8,781,564 B2 | 7/2014 | Kinnunen |
| 8,876,688 B2 | 11/2014 | Hyde et al. |
| 8,897,522 B2 | 11/2014 | Mestha et al. |
| 8,903,491 B2 | 12/2014 | Hopper et al. |
| 8,956,290 B2 | 2/2015 | Gilley et al. |
| 8,972,013 B2 | 3/2015 | Maschino |
| 8,986,206 B2 | 3/2015 | Kim et al. |
| 9,002,427 B2 | 4/2015 | Tupin, Jr. et al. |
| 9,020,185 B2 | 4/2015 | Mestha et al. |
| 9,027,552 B2 | 5/2015 | Angelico et al. |
| 9,028,258 B2 | 5/2015 | Burdea |
| 9,035,778 B2 | 5/2015 | Howie et al. |
| 9,070,267 B2 | 6/2015 | Hanson et al. |
| 9,089,760 B2 | 7/2015 | Tropper et al. |
| 9,106,307 B2 | 8/2015 | Molettiere et al. |
| 9,128,305 B2 | 9/2015 | Honore et al. |
| 9,132,275 B2 | 9/2015 | Yu et al. |
| 9,135,347 B2 | 9/2015 | Damman et al. |
| 9,161,698 B2 | 10/2015 | Zhang et al. |
| 9,168,017 B2 | 10/2015 | Ward et al. |
| 9,171,196 B2 | 10/2015 | Wang et al. |
| 9,173,615 B2 | 11/2015 | Katra et al. |
| 9,180,140 B2 | 11/2015 | Lundberg et al. |
| 9,185,353 B2 | 11/2015 | Mestha et al. |
| 9,204,836 B2 | 12/2015 | Bender et al. |
| 9,220,440 B2 | 12/2015 | Addison et al. |
| 9,232,894 B2 | 1/2016 | Tesanovic et al. |
| 9,232,897 B2 | 1/2016 | Thakur et al. |
| 9,232,910 B2 | 1/2016 | Alshaer et al. |
| 9,247,884 B2 | 2/2016 | Yuen et al. |
| 9,248,306 B2 | 2/2016 | Joo et al. |
| 9,250,104 B2 | 2/2016 | Greiner et al. |
| 9,262,772 B2 | 2/2016 | Stivoric et al. |
| 9,265,477 B2 | 2/2016 | Yang et al. |
| 9,268,908 B2 | 2/2016 | Ashdown et al. |
| 9,286,789 B2 | 3/2016 | Park et al. |
| 9,294,898 B2 | 3/2016 | Shakima et al. |
| 9,333,350 B2 | 5/2016 | Rise et al. |
| 9,390,229 B1 | 7/2016 | Kahn |
| 9,665,873 B2 | 5/2017 | Ackland et al. |
| 10,172,517 B2 | 1/2019 | Jain et al. |
| 10,362,998 B2 | 7/2019 | Jain et al. |
| 10,420,514 B2 | 9/2019 | Jain et al. |
| 2004/0006492 A1 | 1/2004 | Watanage |
| 2005/0070809 A1 | 3/2005 | Acres |
| 2005/0267541 A1 | 12/2005 | Scheiner et al. |
| 2006/0173663 A1 | 8/2006 | Langheier |
| 2006/0218007 A1 | 9/2006 | Bjorner et al. |
| 2007/0024946 A1 | 2/2007 | Panasyuk et al. |
| 2007/0179350 A1 | 8/2007 | Nadeau |
| 2007/0185391 A1 | 8/2007 | Morgan |
| 2007/0207437 A1 | 9/2007 | Sachdeva et al. |
| 2008/0150714 A1 | 6/2008 | Bauer et al. |
| 2009/0058660 A1 | 3/2009 | Torch |
| 2009/0076343 A1 | 3/2009 | James et al. |
| 2009/0234406 A1 | 9/2009 | Shuros et al. |
| 2009/0247831 A1 | 10/2009 | Schechter |
| 2009/0271347 A1 | 10/2009 | Hyde et al. |
| 2009/0312151 A1 | 12/2009 | Thieberger et al. |
| 2009/0312658 A1* | 12/2009 | Thieberger .......... A63B 24/0087 600/520 |
| 2010/0009328 A1 | 1/2010 | Nadeau |
| 2010/0249531 A1 | 9/2010 | Hanlon et al. |
| 2010/0256512 A1 | 10/2010 | Sullivan |
| 2010/0292599 A1 | 11/2010 | Oleson et al. |
| 2010/0292600 A1 | 11/2010 | Dibenedetto et al. |
| 2010/0298899 A1 | 11/2010 | Donnellly et al. |
| 2011/0270049 A1 | 11/2011 | Katra et al. |
| 2011/0275942 A1 | 11/2011 | Stahmann et al. |
| 2011/0295084 A1 | 12/2011 | Thakur et al. |
| 2012/0010504 A1 | 1/2012 | Furlan |
| 2012/0029936 A1 | 2/2012 | Hanoun |
| 2012/0109243 A1 | 5/2012 | Hettrick et al. |
| 2012/0145152 A1 | 6/2012 | Lain et al. |
| 2012/0157856 A1 | 6/2012 | An et al. |
| 2012/0253207 A1 | 10/2012 | Sarkar et al. |
| 2012/0259649 A1 | 10/2012 | Mallon et al. |
| 2012/0270199 A1 | 10/2012 | Malik |
| 2012/0290266 A1 | 11/2012 | Jain et al. |
| 2013/0024212 A1 | 1/2013 | Atakhorrami et al. |
| 2013/0079646 A1 | 3/2013 | Bhunia et al. |
| 2013/0092165 A1 | 4/2013 | Wondka |
| 2013/0197381 A1 | 8/2013 | Charlton et al. |
| 2013/0209977 A1 | 8/2013 | Lathan et al. |
| 2013/0261479 A1 | 10/2013 | Kemppainen et al. |
| 2013/0281798 A1 | 10/2013 | Rau et al. |
| 2014/0006041 A1 | 1/2014 | Steinhauer et al. |
| 2014/0051047 A1 | 2/2014 | Bender et al. |
| 2014/0051941 A1 | 2/2014 | Messerschmidt |
| 2014/0052475 A1 | 2/2014 | Madan et al. |
| 2014/0058745 A1 | 2/2014 | Ji et al. |
| 2014/0061047 A1 | 3/2014 | Stich et al. |
| 2014/0081432 A1 | 3/2014 | Kingon et al. |
| 2014/0100822 A1 | 4/2014 | Hiltner |
| 2014/0107500 A1 | 4/2014 | Stamatopoulos et al. |
| 2014/0112559 A1 | 4/2014 | Freeman et al. |
| 2014/0114147 A1 | 4/2014 | Romesburg |
| 2014/0149465 A1 | 5/2014 | Kannan et al. |
| 2014/0155705 A1 | 6/2014 | Papadopoulos |
| 2014/0155773 A1 | 6/2014 | Stamatopoulos et al. |
| 2014/0171776 A1 | 6/2014 | Lin et al. |
| 2014/0172442 A1 | 6/2014 | Broderick et al. |
| 2014/0228649 A1 | 8/2014 | Rayner et al. |
| 2014/0243686 A1 | 8/2014 | Kimmel |
| 2014/0267668 A1 | 9/2014 | Ignatovich et al. |
| 2014/0276549 A1 | 9/2014 | Osorio |
| 2014/0344208 A1 | 11/2014 | Ghasemzadeh |
| 2014/0371604 A1 | 12/2014 | Katra et al. |
| 2015/0004575 A1* | 1/2015 | Rath .................. G06F 19/3481 434/236 |
| 2015/0011361 A1 | 1/2015 | Boyette et al. |
| 2015/0031965 A1 | 1/2015 | Visvanathan et al. |
| 2015/0038854 A1 | 2/2015 | Zhang et al. |
| 2015/0065825 A1 | 3/2015 | Utley et al. |
| 2015/0065898 A1 | 3/2015 | Prstojevich et al. |
| 2015/0099952 A1 | 4/2015 | Lain et al. |
| 2015/0106020 A1 | 4/2015 | Chung et al. |
| 2015/0125832 A1 | 5/2015 | Tran |
| 2015/0141767 A1 | 5/2015 | Rogers et al. |
| 2015/0186609 A1 | 7/2015 | Utter, II |
| 2015/0202492 A1 | 7/2015 | Domansky et al. |

(56) References Cited

U.S. PATENT DOCUMENTS

| | | | |
|---|---|---|---|
| 2015/0213217 A1 | 7/2015 | Amarasingham et al. | |
| 2015/0216477 A1* | 8/2015 | Sayegh | A61B 8/0858 |
| | | | 600/442 |
| 2015/0269851 A1 | 9/2015 | Lee et al. | |
| 2015/0286857 A1 | 10/2015 | Kim et al. | |
| 2015/0302161 A1 | 10/2015 | Van Dooren et al. | |
| 2015/0305675 A1 | 10/2015 | Miller et al. | |
| 2015/0305683 A1 | 10/2015 | Friat Filing et al. | |
| 2015/0317438 A1 | 11/2015 | Ingrassia, Jr. et al. | |
| 2015/0339363 A1 | 11/2015 | Moldoveanu | |
| 2015/0352147 A1 | 12/2015 | Lundberg et al. | |
| 2015/0359845 A1 | 12/2015 | Marban et al. | |
| 2015/0370993 A1 | 12/2015 | Moturu et al. | |
| 2015/0370994 A1 | 12/2015 | Madan et al. | |
| 2015/0374289 A1 | 12/2015 | Teller et al. | |
| 2015/0379477 A1 | 12/2015 | Junqua et al. | |
| 2016/0008957 A1 | 1/2016 | Kaur et al. | |
| 2016/0019915 A1* | 1/2016 | Khan | G10L 19/018 |
| | | | 704/239 |
| 2016/0022193 A1 | 1/2016 | Rau et al. | |
| 2016/0045168 A1 | 2/2016 | Storer et al. | |
| 2016/0058336 A1 | 3/2016 | Blahnik et al. | |
| 2016/0063205 A1 | 3/2016 | Moturu et al. | |
| 2016/0091922 A1 | 3/2016 | Nazzaro et al. | |
| 2016/0317044 A1 | 3/2016 | Wu | |
| 2016/0235354 A1* | 8/2016 | Weiler | A61B 5/4878 |
| 2016/0328534 A1* | 11/2016 | Kawai | A47C 31/00 |
| 2016/0345841 A1 | 12/2016 | Jang et al. | |
| 2016/0354636 A1 | 12/2016 | Jang et al. | |
| 2017/0017774 A1 | 1/2017 | Skoda | |
| 2017/0245759 A1 | 8/2017 | Jain et al. | |
| 2017/0245805 A1 | 8/2017 | Jain et al. | |
| 2017/0245808 A1 | 8/2017 | Jain et al. | |
| 2017/0249437 A1 | 8/2017 | Jain et al. | |
| 2017/0282011 A1 | 10/2017 | Jang et al. | |
| 2017/0296104 A1 | 10/2017 | Ryan et al. | |
| 2019/0000378 A1 | 1/2019 | Osorio | |

FOREIGN PATENT DOCUMENTS

| | | | |
|---|---|---|---|
| EP | 0559847 A1 | 9/1993 | |
| EP | 1192971 A2 | 8/2001 | |
| EP | 1667578 A1 | 9/2004 | |
| EP | 2739207 A1 | 6/2014 | |
| EP | 2897067 A1 | 7/2015 | |
| KR | 20000006830 A | 2/2000 | |
| KR | 100545772 B1 | 1/2006 | |
| KR | 20060092557 A | 8/2006 | |
| KR | 20100001928 A | 1/2010 | |
| KR | 20130010207 A | 1/2013 | |
| RU | 2462985 C1 | 10/2012 | |
| WO | 9216258 A1 | 10/1992 | |
| WO | 01008755 A1 | 2/2001 | |
| WO | 02018019 A1 | 3/2002 | |
| WO | 2011032132 A2 | 3/2011 | |
| WO | 2013036853 A2 | 3/2013 | |
| WO | 2014147496 A1 | 9/2014 | |
| WO | WO-2015107744 A1 * | 7/2015 | G06Q 50/22 |
| WO | 2015178637 A1 | 11/2015 | |
| WO | 2016004117 A1 | 1/2016 | |
| WO | 2016049425 A1 | 3/2016 | |

OTHER PUBLICATIONS

Guerra, M. et al., "Chronotropic incompetence in persons with down syndrome," Archives of Physical Medicine and Rehabilitation, vol. 8, No. 11, Nov. 1, 2003, pp. 160-1608.

Wilkoff, B.L. et al., "A Mathematical Model of the Cardiac Chronotropic Response to Exercise," Journal of Cardiovascular Electrophysiol, Futura Publishing Co., vol. 3, No. 3, Jun. 1, 1989, pp. 176-180.

"Screening/Evaluation," Community Care of North Carolina, Sep. 2015, 6 pg.

Saeb et al., "Mobile Phone Sensor Correlates of Depressive Symptom Severity in Daily-Life Behaviour: An Exploratory Study," In J. Med. Internet Res., vol. 17, No. 7, e175, Jul. 2015, 20 pg.

EPO Appln. EP17756857.3, Office Action, dated Jun. 14, 2019, 5 pg.

EPO Appln. EP17756862.3, Extended European Search Report, dated Feb. 5, 2019, 11 pg.

EPO Appln. EP17756850.8, Extended European Search Report, dated Feb. 6, 2019, 11 pg.

U.S. Appl. No. 15/296,347, Non-Final Office Action, dated Aug. 28, 2019, 19 pg.

U.S. Appl. No. 15/436,920, Non-Final Office Action, dated Mar. 7, 2018, 11 pg.

Int'l. Appln. No. PCT/KR2017/002043, Int'l. Search Report, dated Apr. 28, 2017, 3 pg.

Int'l. Appln. No. PCT/KR2017/002043, Written Opinion, dated Apr. 28, 2017, 8 pg.

Int'l. Appln. No. PCT/KR2016/014583A1, Int'l. Search Report and Written Opinion, dated Mar. 14, 2017, 11 pg.

Int'l. Appln. No. PCT/KR2017/002055, Int'l. Search Report and Written Opinion, dated May 29, 2017 11 pg.

Int'l. Appln. No. PCT/KR2017/002039, Int'l. Search Report, dated May 23, 2017, 3 pg.

Int'l. Appln. No. PCT/KR2017/002039, Written Opinion, dated May 23, 2017, 3 pg.

Int'l. Appln. No. PCT/KR2017/002055, Int'l. Search Report and Written Opinion, dated May 29, 2017, 13 pg.

Int'l. Appln. No. PCT/KR2017/002067, Int'l Search Report, dated May 29, 2017, 8 pg.

Int'l. Appln. No. PCT/KR2017/002067, Written Opinion, dated May 29, 2017.

Lee, J. et al., "Atrial Fibrillation Detection using a Smart Phone," In 34th Annual Int'l. Conf. of the IEEE Engineering in Medicine and Biology Society (EMBC), Sep. 1, 2012, pp. 1177-1180.

Melzer, C. et al, Predictors of Chronotropic Incompetence in the Pacemaker Patient Population, In Europace, vol. 8, No. 1, Jan. 2006. pp. 70-75.

Melzer, C. et al., "Chronotropic Incompetence: a Never-Ending Story," In Europace, vol. 12, No. 4, Apr. 2010, pp. 464-465.

U.S. Appl. No. 15/436,054, Notice of Allowance, dated Mar. 11, 2019, 11 pg.

EP Appln. EP17756857.3, Extended European Search Report, dated Jan. 2, 2019, 7 pg.

EP Appln. EP16891765.6, Extended European Search Report, dated Jan. 7, 2019, 9 pg.

U.S. Appl. No. 15/436,054, Non-Final Office Action, dated Aug. 14, 2018, 14 pg.

U.S. Appl. No. 15/436,920, Notice of Allowance, dated Aug. 29, 2018, 8 pg.

U.S. Appl. No. 15/296,689, Restriction Requirement, dated Aug. 28, 2018, 7 pg.

U.S. Appl. No. 15/296,689, Non-Final Office Action, dated Nov. 16, 2018, 12 pg.

U.S. Appl. No. 15/296,347, Final Office Action, dated Jan. 28, 2020, 12 pg.

U.S. Appl. No. 15/296,689, Notice of Allowance, dated May 14, 2019, 8 pg.

Ben-Zeev et al., "Next-Generation Psychiatric Assessment: Using Smartphone Sensors to Monitor Behavior and Mental Health," Psychiatr Rehabil J., Sep. 2015, vol. 38, No. 3, pp. 218-226.

U.S. Appl. No. 15/296,347, Non-Final Office Action, dated Feb. 3, 2021, 16 pg.

EP Appln. 17756853.2, Communication Pursuant to Article 94(3), dated Jan. 11, 2021, 12 pg.

Dickerson et al., "Empath: A continuous Remote Emotional Health Monitoring System for Depressive Illness," Wireless Health '11, Oct. 10-13, 2011, 10 PG.

U.S. Appl. No. 15/296,347, Final Office Action, dated Apr. 30, 2021, 15 pg.

* cited by examiner

SENSOR ASSISTED EVALUATION OF HEALTH AND REHABILITATION

CROSS-REFERENCE TO RELATED APPLICATIONS

This application claims the benefit of U.S. Provisional Patent Application No. 62/300,042 filed on Feb. 25, 2016, U.S. Provisional Patent Application No. 62/300,028 filed on Feb. 25, 2016, and U.S. Provisional Patent Application No. 62/300,038 filed on Feb. 25, 2016, each being fully incorporated herein by reference.

TECHNICAL FIELD

This disclosure relates to sensor assisted evaluation of health related quality of life and rehabilitation program compliance.

BACKGROUND

Health-related quality of life, also referred to as "HRQOL," is a measure of the impact of health status of an individual on the individual's quality of life. HRQOL is a multi-dimensional measure that relates to various domains such as physical, mental, emotional, and social functioning of the individual. To the extent that HRQOL can be estimated, such techniques involve the administration of questionnaires to individuals. Often, the questionnaires include a large number of questions resulting in a burdensome process that an individual is unlikely to complete.

Using questionnaires also involves a high degree of subjectivity. The effectiveness of a questionnaire in determining HRQOL depends largely upon the subjectivity of the individual answering the questions. The effectiveness of the questionnaire is also dependent upon the individual's ability to accurately remember conditions probed by the questionnaire, the individual's ability to rank particular experiences and/or health-related conditions, and the willingness of the individual to be open and honest in providing responses.

While HRQOL may be estimated for a variety of individuals including those that are considered healthy, another aspect of HRQOL pertains to individuals recovering from severe medical conditions. In cases where an individual is recovering from a severe medical condition or event, the HRQOL achievable by the individual subsequent to the event often depends heavily upon whether the individual participates in, and complies with, a rehabilitation program. At present, assessments of whether an individual complies with a rehabilitation program is a manual and subjective undertaking performed by medical personnel.

SUMMARY

One or more embodiments are directed to systems and/or apparatus for evaluating health-related quality of life (HRQOL). In one aspect, a system can include a sensor adapted to generate sensor data for a user, a memory adapted to store the sensor data, and a processor coupled to the sensor and the memory. The processor is configured to initiate executable operations including determining a first biological marker for the user from the sensor data, wherein the first biological marker is indicative of a first dimension of HRQOL, performing speech analysis on user provided speech to determine a second biological marker indicative of a second dimension of HRQOL, and comparing the first biological marker and the second biological marker with a baseline for the first biological marker and a baseline for the second biological marker, respectively. The processor is further configured to initiate executable operations including outputting a result of the comparing.

One or more embodiments are directed to methods of evaluating HRQOL. In one aspect, a method can include receiving, using a processor, sensor data for a user, determining, using the processor, a first biological marker for the user from the sensor data, wherein the first biological marker is indicative of a first dimension of HRQOL, and performing, using the processor, speech analysis on user provided speech to determine a second biological marker indicative of a second dimension of HRQOL. The method can also include comparing, using the processor, the first biological marker and the second biological marker with a baseline for the first biological marker and a baseline for the second biological marker, respectively, and outputting, using the processor, a result of the comparing.

One or more embodiments are directed to computer program products for evaluating HRQOL. In one aspect, a computer program product includes a computer readable storage medium having program code stored thereon. The program code is executable by a processor to perform executable operations. The executable operations can include receiving sensor data for a user, determining a first biological marker for the user from the sensor data, wherein the first biological marker is indicative of a first dimension of HRQOL, and performing speech analysis on user provided speech to determine a second biological marker indicative of a second dimension of HRQOL. The executable operations can include comparing the first biological marker and the second biological marker with a baseline for the first biological marker and a baseline for the second biological marker, respectively, and outputting a result of the comparing.

One or more embodiments are directed to systems and/or apparatus for evaluating rehabilitation compliance. In one aspect, a system can include a sensor adapted to generate sensor data for a patient, a memory adapted to store the sensor data, and a processor, coupled to the sensor and the memory. The processor is configured to initiate executable operations including determining a plurality of biological markers from the sensor data collected over a time period corresponding to a rehabilitation program, wherein the plurality of biological markers are correlated with dimensions of domains including exercise training, self-management, and psychosocial health of the patient. The processor is also configured to initiate executable operations including comparing the plurality of biological markers with baselines for the plurality of biological markers and outputting results of the comparing, wherein the results are correlated with the dimensions of the domains.

One or more embodiments are directed to methods of evaluating rehabilitation compliance. In one aspect, a method can include receiving, using a processor, sensor data for a patient, determining a plurality of biological markers from the sensor data collected over a time period corresponding to a rehabilitation program, wherein the plurality of biological markers are correlated with dimensions of domains including exercise training, self-management, and psychosocial health of the patient. The method can include comparing the plurality of biological markers with baselines for the plurality of biological markers and outputting results of the comparing, wherein the results are correlated with the dimensions of the domains.

One or more embodiments are directed to computer program products for evaluating rehabilitation compliance.

In one aspect, a computer program product includes a computer readable storage medium having program code stored thereon. The program code is executable by a processor to perform operations including receiving sensor data for a patient, determining a plurality of biological markers from the sensor data collected over a time period corresponding to a rehabilitation program, wherein the plurality of biological markers are correlated with dimensions of domains including exercise training, self-management, and psychosocial health of the patient. The operations can also include comparing the plurality of biological markers with baselines for the plurality of biological markers and outputting results of the comparing, wherein the results are correlated with the dimensions of the domains.

This Summary section is provided merely to introduce certain concepts and not to identify any key or essential features of the claimed subject matter. Many other features and embodiments of the invention will be apparent from the accompanying drawings and from the following detailed description.

BRIEF DESCRIPTION OF THE DRAWINGS

The accompanying drawings show one or more embodiments; however, the accompanying drawings should not be taken to limit the invention to only the embodiments shown. Various aspects and advantages will become apparent upon review of the following detailed description and upon reference to the drawings.

DETAILED DESCRIPTION

Figure 1:
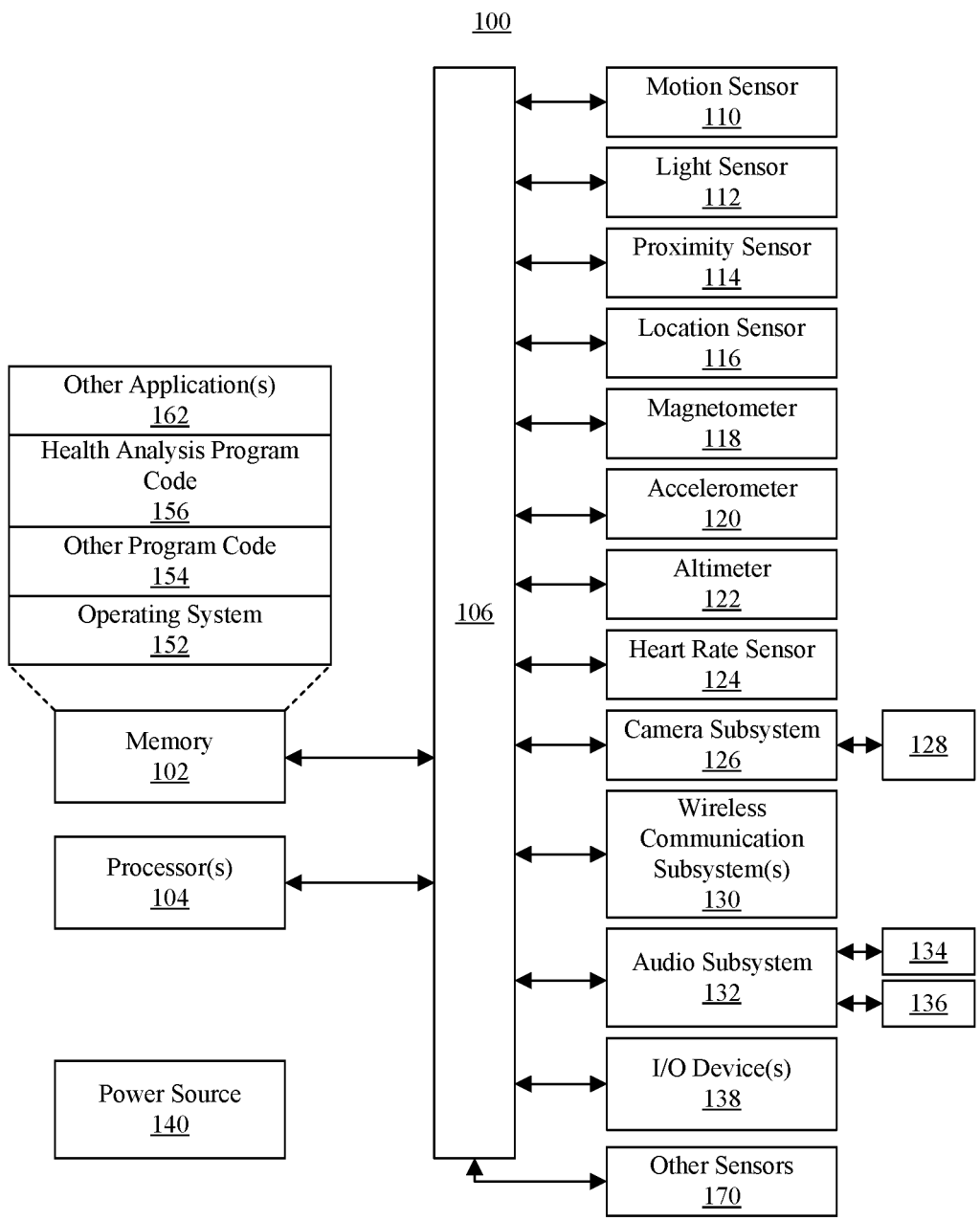
FIG. 1 illustrates an example system in accordance with one or more embodiments described herein.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to sensor assisted evaluation of health related quality of life for and rehabilitation program compliance. In one or more embodiments, a system is adapted to monitor a user using one or more sensors. The system is capable of collecting sensor data for the user over time and in various contexts as described herein. The system is capable of analyzing sensor data to generate one or more baselines for various biological markers.

In an aspect, the biological markers are indicative of different measures of health-related quality of life (HRQOL) for the user. For example, the biological markers derived from the sensor data are indicative of dimensions used to determine HRQOL including, but not limited to, mobility, self-care, and/or usual activities of the user. The system is also capable of deriving one or more biological markers that are indicative of other more subjective measures of HRQOL. As an illustrative example, the system is capable of using speech analysis on user speech in order to detect levels of pain and/or discomfort experienced by the user and/or levels of anxiety and/or depression experienced by the user.

The system is capable of continually collecting sensor data and determining updated states for the various biological markers. Accordingly, the system is capable of comparing the biological markers, e.g., the updated states thereof, with the baselines for the corresponding biological markers. Any changes detected by the system may be recorded and/or otherwise output, e.g., stored in a memory or other data storage device. In one or more embodiments, results from the comparisons performed may be output as an HRQOL score.

Further aspects of the inventive arrangements are described below in greater detail with reference to the figures. For purposes of simplicity and clarity of illustration, elements shown in the figures are not necessarily drawn to scale. For example, the dimensions of some of the elements may be exaggerated relative to other elements for clarity. Further, where considered appropriate, reference numbers are repeated among the figures to indicate corresponding, analogous, or like features.

FIG. 1 illustrates an example system 100 in accordance with one or more embodiments described within this disclosure. System 100 can include a memory 102, one or more processors 104 (e.g., image processors, digital signal processors, data processors, etc.), and interface circuitry 106. In one aspect, memory 102, processor(s) 104, and/or interface circuitry 106 are implemented as separate components. In another aspect, memory 102, processor(s) 104, and/or interface circuitry 106 are integrated in one or more integrated circuits. The various components in system 100, for example, can be coupled by one or more communication buses, I/O subsystems, or signal lines (e.g., interconnects and/or wires) represented as interface circuitry 106. In one aspect, memory 102 may be coupled to interface circuitry 106 via a memory interface (not shown).

Sensors, devices, subsystems, and/or input/output (I/O) devices can be coupled to interface circuitry 106 to facilitate the functions and/or operations described within this disclosure including the generation of sensor data. The various sensors, devices, subsystems, and/or I/O devices may be coupled to interface circuitry 106 directly or through one or more intervening I/O controllers (not shown).

For example, motion sensor 110, light sensor 112 (e.g., an ambient light sensor), and proximity sensor 114 can be coupled to interface circuitry 106 to facilitate orientation, lighting, and proximity functions, respectively, of system 100. Location sensor 116 (e.g., a GPS receiver and/or processor) can be connected to interface circuitry 106 to provide geo-positioning sensor data. Electronic magnetometer 118 (e.g., an integrated circuit chip) can be connected to interface circuitry 106 to provide sensor data that can be used to determine the direction of magnetic North for purposes of directional navigation. Accelerometer 120 can be connected to interface circuitry 106 to provide sensor data that can be used to determine change of speed and direction of movement of the system in 3-dimensions. Altimeter 122 (e.g., an integrated circuit) can be connected to interface circuitry 106 to provide sensor data that can be used to determine altitude. Heart rate sensor 124 can be connected to interface circuitry 106 to generate sensor data and facilitate measurement of a heartbeat and the determination of a heart rate.

Camera subsystem 126 can be coupled to an optical sensor 128. Optical sensor 128 can be implemented using any of a variety of technologies. Examples of optical sensor 128 can include, but are not limited to, a charged coupled device (CCD), a complementary metal-oxide semiconductor (CMOS) optical sensor, etc. Camera subsystem 126 and optical sensor 128 can be used to facilitate camera functions, such as recording images and/or video clips (hereafter "image data"). In one aspect, image data is a subset of sensor data.

Communication functions can be facilitated through one or more wireless communication subsystems 130. Wireless communication subsystems 130 can include, but are not limited to, radio frequency receivers and transmitters, optical (e.g., infrared) receivers and transmitters, and so forth. The specific design and implementation of wireless communication subsystems 130 can depend on the particular type of system 100 implemented and/or the communication network(s) over which system 100 is intended to operate.

For purposes of illustration, wireless communication subsystem(s) 130 may be designed to operate over one or more mobile networks, WiFi networks which may include WiMax network(s), short range wireless networks (e.g., Bluetooth networks), and/or any combination of the foregoing. In another aspect, wireless communication subsystem(s) 130 are capable of implementing hosting protocols such that system 100 can be configured as a base station for other wireless devices.

Audio subsystem 132 can be coupled to a speaker 134 and a microphone 136 to facilitate voice-enabled functions, such as voice recognition, voice replication, digital recording, speech and/or audio processing, and telephony functions. Audio subsystem 132 is capable of generating audio type sensor data. In one or more embodiments, microphone 136 may be utilized as a respiratory sensor.

I/O devices 138 can be coupled to interface circuitry 106. Examples of I/O devices 138 can include, but are not limited to, display devices, touch sensitive display devices, track pads, keyboards, pointing devices, communication ports (e.g., USB ports), network adapters, buttons or other physical controls, and so forth. A touch sensitive device such as a display screen and/or a pad is configured to detect contact, movement, breaks in contact, etc., using any of a variety of touch sensitivity technologies. Example touch sensitive technologies include, but are not limited to, capacitive, resistive, infrared, and surface acoustic wave technologies, other proximity sensor arrays or other elements for determining one or more points of contact with a touch sensitive device, etc. One or more of I/O devices 138 may be adapted to control functions of sensors, subsystems, and such of system 100.

System 100 further includes a power source 140. Power source 140 is capable of providing electrical power to the various elements of system 100. In an embodiment, power source 140 is implemented as one or more batteries. The batteries may be implemented using any of a variety of different battery technologies whether disposable (e.g., replaceable) or rechargeable. In another embodiment, power source 140 is configured to obtain electrical power from an external source and provide power (e.g., DC power) to the elements of system 100. In the case of a rechargeable battery, power source 140 further may include circuitry that is capable of charging the battery or batteries when coupled to an external power source.

Memory 102 can include random access memory (e.g., volatile memory) and/or non-volatile memory, such as one or more magnetic disk storage devices, one or more optical storage devices, flash memory, etc. Memory 102 can store operating system 152, such as LINUX, UNIX, a mobile operating system, an embedded operating system, etc. Operating system 152 may include instructions for handling system services and for performing hardware dependent tasks.

Memory 102 may also store other program code 154. Examples of other program code 154 may include instructions that facilitate communicating with one or more additional devices, one or more computers and/or one or more servers; graphic user interface operations; sensor-related operations; phone-related operations; electronic-messaging related operations; Web browsing-related operations; media processing-related operations; GPS and navigation-related operations; security operations; camera-related operations including Web camera and/or Web video operations; and so forth. Memory 102 may also store one or more other application(s) 162.

Memory 102 may store health analysis program code 156. In one aspect, health analysis program code 156 is adapted to facilitate evaluation of HRQOL for a user. In another aspect, health analysis program code 156 is adapted to facilitate evaluation of rehabilitation program compliance by a patient. Health analysis program code 156 is capable of analyzing sensor data, detecting biological markers, generating baselines for biological markers, querying a user for input, querying one or more external data sources for information, and performing comparisons of sensor data, user input, and/or data obtained from the external data sources with biological markers and/or baselines thereof. Further aspects of operations performed through execution of health analysis program code 156 are described herein with reference to the remaining figures.

Memory 102 may also store various types of data (not shown) such as sensor data, biological marker data, baseline data including baselines for one or more biological markers, data obtained by way of received user input(s), data obtained by way of querying one or more external data sources, etc.

The various types of instructions and/or program code described are provided for purposes of illustration and not limitation. The program code may be implemented as separate software programs, procedures, or modules. Memory 102 can include additional instructions or fewer instructions. Furthermore, various functions of system 100 may be implemented in hardware and/or in software, including in one or more signal processing and/or application specific integrated circuits.

Program code stored within memory 102 and any data items used, generated, and/or operated upon by system 100 are functional data structures that impart functionality when employed as part of the system. Further examples of functional data structures include, but are not limited to, sensor data, data obtained via user input, data obtained via querying external data sources, biological marker data, baseline data, and so forth. The term "data structure" refers to a physical implementation of a data model's organization of data within a physical memory. As such, a data structure is formed of specific electrical or magnetic structural elements in a memory. A data structure imposes physical organization on the data stored in the memory as used by a processor.

In one or more embodiments, one or more of the various sensors and/or subsystems described with reference to system 100 may be separate devices that are coupled or communicatively linked to system 100 through wired or wireless connections. For example, one or more or all of motion sensor 110, light sensor 112, proximity sensor 114, location sensor 116, electronic magnetometer 118, accelerometer 120, altimeter 122, heart rate sensor 124, camera subsystem 126, audio subsystem 132, and so forth may be implemented as separate systems or subsystems that couple to system 100 by way of I/O devices 138 and/or wireless communication subsystem(s) 130.

One or more of the sensors may be worn directly by the user and provide data to system 100 via a wired or wireless connection. Examples of additional sensors that are not illustrated in FIG. 1, but which may be used and/or worn by a user to provide sensor data to system 100 can include, but are not limited to electrocardiography (ECG) sensors, photoplethysmography (PPG) sensors, gyroscopes, respiratory sensors, galvanic skin response (GSR) sensors, etc. These additional sensors are represented in FIG. 1 by "other sensors" block 170. In one or more embodiments, sensors and/or subsystems as described herein are configured to generate sensor data that is stored in a memory external to system 100. In that case, system 100, e.g., processors 104, may access the sensor data for use and/or analysis as described herein.

System 100 may include fewer components than shown or additional components not illustrated in FIG. 1 depending upon the particular type of system that is implemented. In addition, the particular operating system and/or application(s) and/or other program code included may also vary according to system type. Further, one or more of the illustrative components may be incorporated into, or otherwise form a portion of, another component. For example, a processor may include at least some memory.

System 100 is provided for purposes of illustration and not limitation. A device and/or system configured to perform the operations described herein may have a different architecture than illustrated in FIG. 1. The architecture may be a simplified version of the architecture described in connection with system 100 and include a processor and memory storing instructions. The architecture may include one or more sensors or subsets of sensors as described herein. System 100, or a system similar to system 100, is capable of collecting sensor data using the various sensors of the device or sensors coupled thereto. It should be appreciated, however, that system 100 may include fewer sensors or additional sensors. Within this disclosure, data generated by a sensor is called "sensor data."

Examples implementations of system 100 may include, but are not to limited to, a smart phone or other mobile device or phone, a wearable computing device (e.g., smart watch, fitness tracker, patch, etc.), a dedicated medical device, a computer (e.g., desktop, laptop, tablet computer, other data processing system, etc.), and any suitable electronic device capable of sensing and processing the sensor data. Furthermore, it will be appreciated that embodiments can be deployed as a standalone device or deployed as multiple devices in a distributed client-server networked system. In an example embodiment, a smart watch or fitness tracker may be paired to operate with a mobile phone or other data processing system. The mobile phone may or may not be configured to interact with a remote server and/or computer system.

Figure 2:
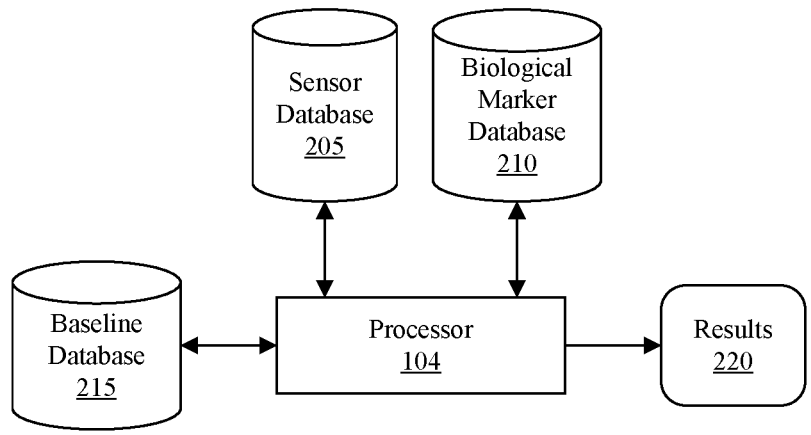
FIG. 2 illustrates an example of processing sensor data for determining biological markers and baselines for biological markers as performed by the system of FIG. 1.

FIG. 2 illustrates an example of processing sensor data for determining biological markers and baselines for biological markers as performed by the system of FIG. 1. Processor 104 of system 100, for example, is capable of storing sensor data within a sensor database 205, detected biological markers and/or updates in states of biological markers within biological marker database 210, and baselines for biological markers (e.g., "baselines") within baseline database 215. In an aspect, sensor database 205, biological marker database 210, and baseline database 215 are stored in memory 102.

It should be appreciated that while certain types of data are described within this disclosure as being stored within databases, the inventive arrangements are not intended to be limited to storing data in one particular format, data storage device, or data structure. Use of databases is for purposes of illustration and description. The various types of data described within this disclosure may be stored in any of a variety of different types of data storage devices using any of a variety of different data structures such as files, markup languages, and so forth.

Sensor database 205 is adapted to store sensor data generated by the various sensors described herein with reference to FIG. 1. For example, sensor database 205 is capable of storing time-series sensor data for the various types of sensors described in connection with FIG. 1. As such, sensor database 205 can store different types of sensor data, e.g., raw and/or unprocessed sensor data, including, but not limited to, accelerometer data, gyroscope data, altimeter data, audio data (e.g., from a microphone), location data (e.g., from a GPS system, identifying WiFi networks, etc.), accelerometer data, PPG data if available, heart rate data, etc.

Processor 104 is capable of analyzing sensor data from sensor database 205 to generate biological markers stored in biological marker database 210. In one aspect, the system is capable of generating updated states of the biological markers described herein. The updated states of the biological markers (e.g., biological markers) may be stored as time series data. In one aspect, regarding HRQOL, the biological markers determined by processor 104 and for which updated states are determined are indicative, or representative, of various dimensions for measuring HRQOL. In an example, these dimensions include, but are not limited to, physical function of the user, social interaction of the user, psychological function of the user, and disease and treatment related symptoms of the user.

In one or more embodiments, processor 104 is capable of using sensor data from sensor database 205 to determine biological markers that are indicative of state of health of a user for one or more or all dimensions from available, well-proven, medical instruments (e.g., questionnaires). In an embodiment, the biological markers are indicative of dimensions such as mobility, self-care, usual activities, pain/discomfort, and/or anxiety/depression from the EQ-5D. The EQ-5D is a standardized questionnaire designed to measure health status of a user across the dimensions noted. In one aspect, the EQ-5D-3L may be used which receives answers to each of the five dimensions at one of three different levels that may range from "no problem," to "some problem," to "severe problem" for each of the noted dimensions. The EQ-5D-3L may be scored using a 1, 2, or 3 for each dimension, where the answer for each dimension is concatenated resulting in a 5 digit score. In another aspect, the EQ-5D-5L is used which allows for five different levels of response in each of the five dimensions thereby providing greater detail and granularity in measuring health status of an individual. The EQ-5D-5L may be scored using a 1, 2, 3, 4, or 5 for each dimension, where the answer for each dimension is concatenated resulting in a 5 digit score with much greater range compared to the EQ-5D-3L.

Baseline database 215 stores baselines for the biological markers used to evaluate HRQOL. For example, for each different biological marker and/or combination of biological markers for which an updated state is determined and stored in biological marker database 210, a corresponding baseline of the biological marker(s) and/or combination of biological markers is stored in baseline database 215.

In an embodiment, baseline database 215 stores baselines. In one aspect, a baseline specifies a value or values (e.g., a time series of values such as sensor data from one or more sensors) that is recognized or indicates a particular biological marker or biological markers. In an aspect, a baseline may include additional information interpreting the sensor data, e.g., tags or other metadata. For example, a baseline of accelerometer sensor data may be tagged or include metadata indicating the particular actions performed by the user as determined from the accelerometer data. A baseline further may include one or more user inputs such as a time series of data received from the user. The baselines are measured while the user is in a known state that may be used as a point of reference and/or comparison. For example, the known state may be prior to a medical event such as a surgery, subsequent to a medical event such as surgery, prior to the user beginning a medication regimen, while the user is adhering to, or following, a particular medication regimen, prior to a rehabilitation program, etc. The term "medication regimen," as used herein, refers to the overall medication program followed by a user. For example, the medication regimen may specify information such as the particular medication(s) taken by the user, the quantity and/or the concentration of each medication taken by the user, the times of day and/or frequency that the medications are taken by the user, etc. Within this disclosure, the terms "regimen" and "medication regimen" are used interchangeably from time-to-time.

Thus, a baseline for a biological marker, or a set of two or more biological markers, reflects the state of the biological marker(s) for a given, known health state of the user for purposes of comparison with biological markers determined over time from sensor data to detect changes in health status of the user. It should be appreciated that the baselines of one user may differ from the baselines for another different user based upon general health, medical conditions, age, and so forth. In one or more embodiments, the biological markers are determined in real time and/or compared with the baselines in real time.

For purposes of illustration, the following describes biological markers that processor 104 is capable of determining from sensor data as a user or patient carries or wears a system and/or sensors as described herein. Biological markers determined by processor 104 may be stored in biological marker database 210. As discussed, a baseline for each biological marker may also be generated and stored in baseline database 215 for purposes of comparison. Within the description below, the biological markers are also correlated with (e.g., indicative of) particular dimensions of the EQ-5D.

In an embodiment, processor 104 is capable of processing sensor data to generate one or more biological markers that are indicative of mobility. Regarding mobility, for example, processor 104 is capable of identifying one or more different types of physical activities that the user performs based upon sensor data. For example, processor 104 is capable of identifying activities such as jogging, sitting, standing, going up stairs, going down stairs, walking, etc., from accelerometer sensor data, gyroscope data, altitude data, and/or location data. Thus, processor 104 is capable of determining a current state of the user's mobility based upon the particular activities detected from the sensor data for different periods of time.

In an embodiment, processor 104 is capable of processing sensor data to generate one or more biological markers that are indicative of self-care. Regarding self-care, for example, processor 104 is capable of identifying one or more different types of physical activities that the user performs based upon sensor data as described. For example, processor 104 is capable of identifying activities including, but not limited to, washing and/or bathing, dressing, and so forth. It should be appreciated that, using available techniques and/or methods, a wide variety of user activities may be determined or identified from an analysis of sensor data generated from inertial sensors with or without GPS (e.g., location) data. Thus, processor 104 is capable of determining a current state of the user's self-care in terms of the particular types of activities detected from the sensor data over time.

In an embodiment, processor 104 is capable of processing sensor data to generate one or more biological markers that are indicative of usual activities engaged in by the user. "Usual activities" refer to daily activities performed by the user and/or patient that involve travel from place to place, e.g., from one room to another, from one location such as home to another such as work. For example, processor 104 is capable of identifying one or more different types of activities that the user performs based upon accelerometer sensor data, gyroscope data, altitude data, and/or location data. Processor 104 is capable of identifying activities such as leaving home to go to work, going to the gym, going to the grocery store, returning home, and so forth. Thus, processor 104 is capable of determining biological markers such as movement to and from various places at particular times and/or on particular days from the sensor data over time.

In an embodiment, processor 104 is capable of processing sensor data to generate one or more biological markers that are indicative of pain/discomfort experienced by the user. Regarding pain/discomfort, for example, processor 104 is capable of evaluating the user's gait. Biological markers such as whether the user's movements are stilted, smooth, free-flowing, etc., are indicative of pain experienced by the user.

Processor 104 is capable of determining another biological marker indicative of pain/discomfort such as stress. Processor 104 is capable of using sensor data, e.g., heart rate sensor data, to detect exposure of the user to stress. When under stress, for example, the user's Autonomic Nervous System (ANS) arousal and valence are typically in the second quadrant of the Circumplex Model of Emotions, which can be determined by heart rate and heart rate variability analysis where both trend down at the same time. In an embodiment, processor 104 is capable of using heart rate and/or heart rate variability from the sensor data to determine whether the user is under stress and/or the amount of stress over time. The addition and use of other sensors such as GSR sensor(s) and GSR sensor data may further improve the determination of valence and arousal.

For example, processor 104 is capable of determining whether the user is subject to stress and whether the amount of stress exceeds a baseline amount of stress based upon heart rate (e.g., energy) and heart rate variability (e.g., mood) of the user both being low (e.g., below a threshold for heart rate and/or a threshold for heart rate variability) at the same time and/or remaining low (concurrently) for at least a minimum amount of time. The threshold(s) may be specific to the user or generalized across one or more different users. The stress biological marker is indicative of pain/discomfort since the user typically experiences increased stress when experiencing increased pain/discomfort. In a further aspect, the biological marker for stress is also indicative of anxiety.

In an embodiment, processor 104 is capable of determining whether the user is experiencing depression. In one or more embodiments, the system is capable of implementing a depression detection process described herein in greater detail in connection with FIGS. 5, 6, and 7. Processor 104 is capable of performing such processes to determine or detect that the user is experiencing depression and the levels thereof.

In an embodiment, processor 104 is capable of receiving one or more speech inputs from the user and performing speech analysis upon the received speech. The speech may be analyzed for various features (biological markers) that are indicative of pain/discomfort and/or anxiety/depression. For example, processor 104 is capable of measurable an acoustic difference in the user's speech, even when speaking the same sequence of words, in cases where the underlying emotion of the user differs. Thus, processor 104 is capable of determining emotional state of the user based upon speech analysis. The emotional state may be used as a biological marker indicative of pain/discomfort and/or anxiety/depression.

As an illustrative example, a user may respond with a verbal response of "I am fine" in a variety of different circumstances ranging from a polite "I am fine" when feeling miserable to a response of "I am fine" when feeling centered in a positive state of mind. There are several well understood physiological reasons behind this phenomenon such as change in the muscle tension controlling voice and respiration due to a change in the balance of the sympathetic and the parasympathetic nervous systems. Processor 104 is capable of determining features of the user's speech such as fundamental frequency, vocal perturbation (short-term variability in sound production), voice quality (e.g., timbre), intensity (e.g., loudness, shimmer), temporal aspects of the speech (e.g., rate of speech), and/or different combinations of one or more of the foregoing similar characteristics (e.g., prosodic features) to detect emotional state of the user and/or patient.

For example, processor 104 is capable of analyzing the features noted above in terms of prosodic features such as statistics of pitch, energy, duration and higher order formants; spectral features such as spectrum centroid, spectrum cut-off frequency, correlation density and mel-frequency energy; and one or more other high-level features. In an embodiment, processor 104 may categorize underlying features in speech as either frame-related features or utterance-related features.

In performing speech analysis as described, processor 104 is capable of operating on recorded audio data of the user's speech (e.g., audio sensor data) and determining biological markers such as rate, intensity, pauses, fundamental frequency, jitter, shimmer, breaks, reduction or jump in pitch, energy spectrum, etc. Based upon these, given an adequately representative baseline model of the biological markers and suitable machine learning techniques such as support vector machines, Hidden Markov Models, K-nearest neighbors, artificial neural networks, Gaussian mixture models etc., processor 104 is capable of outputting a likely emotional state of the user.

In an embodiment, processor 104 need not perform speech recognition, e.g., convert user spoken utterances to text, to perform the speech processing described. In another embodiment, however, processor 104 is capable of performing speech recognition to generate a textual representation of the user's speech. The textual representation, or transcript, of the user's speech may be used for purposes of validating particular dimensions of the EQ-5D.

As discussed, the biological markers may be represented as time-series data. Further, biological markers and baselines thereof may be day specific, time period specific, etc. For example, the determination that a person is going to work as expected may be both a day-specific and time-specific determination since regular or expected trips to and from work are detected at particular times (e.g., to work in mornings and leaving work in afternoons) on weekdays only. In this regard, there may be different baselines for a biological marker for different days of the week, different times of day, etc.

Processor 104 is capable of comparing biological markers with baseline biological markers to detect changes that can be output as results 220. For example, processor 104 is capable of detecting a deviation of one or more biological markers from the baselines of the biological markers and outputting detected deviations. In an embodiment, processor 104 is capable of outputting correlated the detected changes in biological markers with a score for the EQ-5D that may be output for the user as results 220.

Figure 3:
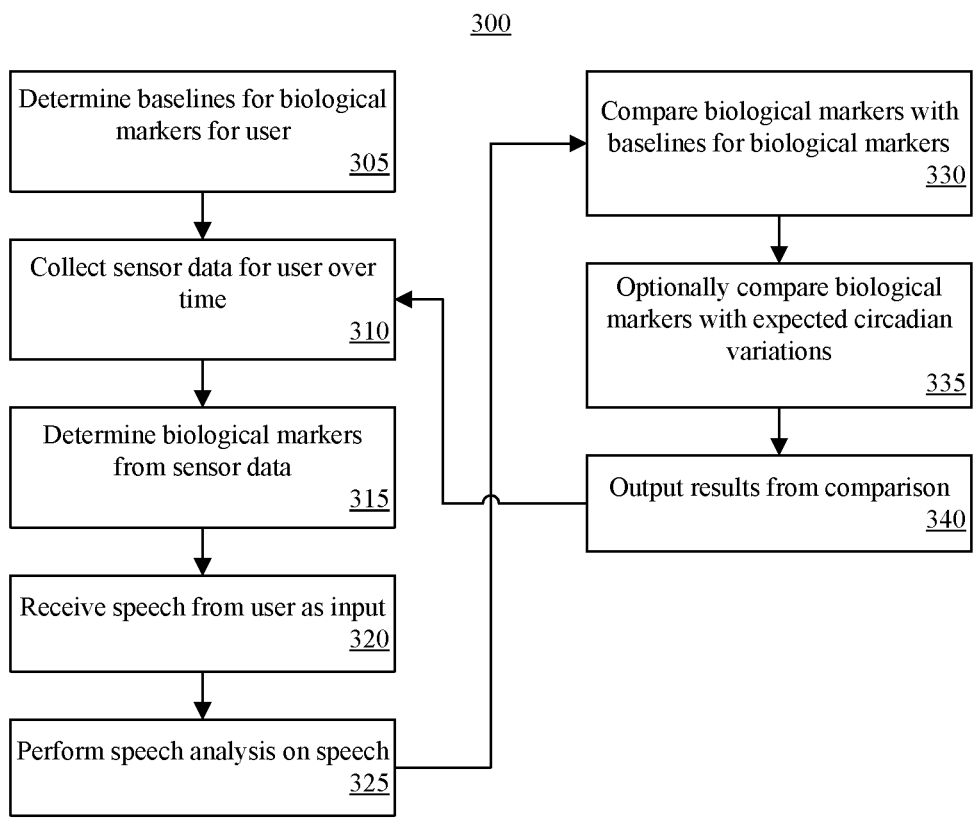
FIG. 3 illustrates an example method of evaluating health-related quality of life (HRQOL).

FIG. 3 illustrates an example method 300 of evaluating HRQOL. Method 300 may be performed using a system the same as or similar to the system described in connection with FIG. 1. Method 300 can be performed to evaluate the HRQOL of a user under any of a variety of conditions whether the user is healthy, for example, or recovering from a medical condition.

Method 300 may begin in block 305 where the system determines baselines for various ones of the biological markers. As discussed, the baselines for the biological markers may be determined while the user is in a known state. The baselines may be determined over a period of time to capture variations in the baselines that may be time period specific, day specific, and so forth. The particular baselines determined may include those described with reference to FIG. 2 relating to the dimensions of mobility, self-care, usual activities, pain/discomfort, and anxiety/depression.

In block 310, the system continues to collect sensor data over time. The sensor data is stored in memory. For example, a user may carry, wear, or otherwise keep a system, device, and/or sensors as described with reference to FIG. 1 on the user's person or with the user throughout the day for purposes of monitoring and collecting sensor data. In block 315, the system analyzes the sensor data and determines biological markers from the sensor data. In an embodiment, the system analyzes the sensor data in order to determine current states of biological markers that are indicative of the dimensions of mobility, self-care, and usual activities.

Though blocks 310 and 315 are shown as individual blocks, it should be appreciated that the system is capable of continually performing blocks 310 and/or 315. For example, the system is adapted to perform one or more operations concurrently, e.g., using multiple processors, using multi-threading and/or multi-tasking, etc. As such, the system is capable of continuing to collect sensor data and determine biological markers over time.

In block 320, the system receives speech as input, e.g., audio sensor data, from the user. In one or more embodiments, the system is capable of prompting the user for information relating to how the user feels. For example, the system is capable of providing a prompt through a user interface such as a graphical user interface, an audio prompt, etc. In an example, the system may prompt the user via a user interface to answer the pain/discomfort and/or the anxiety/depression questions from the EQ-5D. The user may respond using either the 3L or the 5L answer format. In another example, the system may prompt the user through a user interface as to how the user feels in general. The system may prompt the user and/or receive speech from the user at one or more different times per day. In an example, the system receives the speech in the evening. In one or more embodiments, the system is capable of recording user speech at one or more times throughout the day with or without prompting. In either case, the system is capable of recording the user's speech as audio sensor data for purposes of analysis. In an embodiment, the system is also capable of assessing responses from the user for any of the EQ-5D questions, e.g., using sensor data and/or speech analysis.

It should be appreciated that while the EQ-5D is used within this disclosure for purposes of illustration, other instruments may be used in lieu of, or in addition to, the EQ-5D. In this regard, the embodiments described within this disclosure are not intended to be limited to any particular type of instrument or the examples provided. A system configured in accordance with the inventive arrangements described herein is capable of addressing any other HRQOL determination instrument if the user is prompted for a spoken assessment of each dimension to be assessed. The system may perform speech analysis on such user provided spoken responses to determine the quality of the user's response(s).

In block 325, the system performs speech analysis on the speech. The system is capable of determining one or more of the speech-related biological markers for purposes of emotional analysis of the user's voice. As discussed, the resulting emotional state of the user may be used to estimate pain/discomfort and/or the anxiety/depression of the user. In one or more embodiments, the system is also capable of using speech analysis on the user's speech to determine or confirm sensor based assessment(s) of other states of the user that are required by the EQ-5D model (or other instrument). Thus, the speech based analysis can supplement the sensor based analysis for instances where the sensor based measurement(s) provide a probable resolution of the user's state.

For example, an angry emotional state is indicated by a higher fundamental, irregular fluctuations in the contour of the fundamental, higher average intensity, wider intensity range, slightly faster speaking rate, and increased high frequency energy. A happy emotional state is indicated by a higher fundamental, descending and ascending patterns at irregular intervals for the contour of the fundamental, higher average intensity, wider intensity range, normal speaking rate, and increased high frequency energy. A sad emotional state is indicated by a lower fundamental, downward inflections in the contour of the fundamental, lower average intensity, narrower intensity range, slightly lower speaking rate, and decreased high frequency energy. A fearful emotional state is indicated by much higher fundamental, much more irregularity in up-down fluctuations in contour of the fundamental, lower average intensity, narrower intensity range, slightly slower speaking rate, and increased high frequency energy.

In block 330, the system compares the biological markers, e.g., current or updated states of the biological markers, with the baselines for the biological markers. For example, the system is capable of comparing a biological marker indicative of each dimension of the EQ-5D with a corresponding baseline biological marker to determine whether the current state of the biological marker has changed relative to the baseline biological marker. The system is capable of detecting deterioration, improvement, or no change in the current state of the biological marker relative to the baseline.

In comparing emotional states, different emotional states may be ranked or correlated on a scale for pain/discomfort and/or anxiety/depression. For example, the system may detect increased pain/discomfort and/or increased anxiety/depression in response to detecting a change in emotional state from "happy" to "sad" or from "happy" to "fearful."

In performing the comparing, the system is capable of applying any of a variety of statistical processing techniques. In an example, the system is capable of computing the covariance between a biological marker and the baseline for the biological marker. The system is further capable of determining whether the biological marker has changed by at least a threshold amount compared to the baseline.

In block 335, the system is capable of optionally comparing one or more of the biological markers with expected circadian variations. Circadian variations are expected effects on one or more biological markers for different times throughout the day. Biological markers may be expected to increase, decrease, or remain unchanged in accordance with the location in the Circadian cycle that the biological markers are measured. An example of a circadian variation is a pronounced dip in heart rate and blood pressure for persons during the night. Another example of a circadian variation is a corresponding surge of blood pressure in the morning called morning surge reactivity.

In an embodiment, the system is capable of storing baselines indicating expected, or healthy, circadian variations for heart rate and/or blood pressure. The baselines may be stored in a circadian database, for example, or within baseline database 215. The system is capable of determining whether the observed heart rate and/or blood pressure for the user exhibits the expected circadian variation that is indicative of a healthy individual. The system is capable of determining whether observed heart rate and/or blood pressure of the user from sensor data is consistent, e.g., within a threshold amount, for the specified circadian variations over time.

Heart rate may be determined by the system from heart rate sensor data. In an embodiment, the system is capable of measuring blood pressure based upon PPG morphology in the case where the system obtains PPG sensor data. The system, for example, is capable of determining systolic blood pressure for a user based upon the area beneath the curve of a PPG waveform. Larger area corresponds to higher systolic blood pressure.

In block 340, the system is capable of outputting results of the comparing. In one or more embodiments, the system is capable of outputting a notification indicating whether the biological markers changed relative to the baseline, the amount of change, etc. The system is also capable of outputting results of any comparisons performed between biological markers and circadian variations.

In an embodiment, the current state of the biological markers relative to the baselines for the biological markers may be correlated with responses to the EQ-5D-3L or to the EQ-5D-5L for purposes of scoring. For example, regarding the EQ-5D-5L, the baseline biological markers for mobility may be correlated to a particular response such as a "1" (I have no problems in walking about); a "2" (I have slight problems in walking about); "3" (I have moderate problems in walking about); "4" (I have severe problems in walking about); or "5" (I am unable to walk about). The system compares the current state of the biological markers with the baselines to determine whether a change has occurred, the direction of the change (improvement or deterioration), and the amount of the change. The system is capable of selecting a current level of response to the mobility dimension based upon any detected change or lack of change.

For purposes of illustration, consider an example where the baseline biological markers for the mobility dimension are correlated with the a "3." In response to determining that the current state of the biological markers for the mobility dimension improve by a threshold amount, the system determines that the current level response for the user for the mobility corresponds to a "2." In response to determining that the current state of the biological markers for the mobility dimension deteriorates by a threshold amount, the system determines that the current level response for the user for the mobility dimension should be a "4." Deviations by more than the threshold amounts, may cause the system to determine that the level of response for the user should increase or decrease by more than one level. The system is capable of performing a similar process in the case where the EQ-5D-3L is used and performing the above described analysis across the different dimensions.

By performing the comparisons indicated above, the system is capable of generating results over time that indicate the HRQOL for the user. The results may be provided using a traditional scoring for the EQ-5D as described above where levels of responses are rated 1-5 for the EQ-5D-5L or 1-3 for the EQ-5D-3L. The results may be provided in terms of degree of variation from baselines showing improvements, lack of change, deterioration, and/or amounts of such change over time. Further, results may be aggregated over time to indicate the user's HRQOL for a time period such as a week, month, etc.

The example described in connection with FIG. 3 utilizes speech processing to determine emotional state of the user for purposes of estimating the HRQOL of the user. In one or more embodiments, the system is able to incorporate or use a depression detection technique to explicitly determine whether the user is suffering from depression and/or the degree of depression (e.g., changes in depression). The analysis for detecting depression is described herein in greater detail with reference to FIGS. 5, 6, and 7. The explicit depression detection process may be performed in addition to, or in lieu of, the speech processing described herein. For example, speech processing may be used for detecting pain/discomfort, while the depression detection processes described with reference to FIGS. 5, 6, and 7 may be used to detect anxiety/depression.

This disclosure also relates to sensor assisted evaluation of rehabilitation program compliance for a user. In one or more embodiments, a system is adapted to monitor a user, e.g., a patient, using one or more of the various sensors described herein. The system is capable of collecting sensor data for the patient over time and in various contexts. The system is capable of analyzing the sensor data to determine biological markers indicative of one or more domains correlated with rehabilitation compliance. The system is capable of comparing the biological markers determined from the sensor data with baselines for the biological markers to determine whether the patient is compliant and/or has complied with the rehabilitation program.

As an illustrative example, the system is capable of detecting biological markers indicative of particular dimensions in domains such as exercise training, self-management, and psychosocial health. These domains are relevant to determining and evaluating whether a patient is and/or has complied with a rehabilitation program. Within the exercise training domain, for example, the biological markers may be indicative of one or more of dimensions such as target heart rate, length of exercise, time of exercise, warm-up period for exercise, and/or cool-down period for exercise. Within the self-management domain, for example, the biological markers may be indicative of one or more domains such as medication regimen adherence, blood pressure, blood glucose, weight, smoking, fluid intake, and/or sleep. Within psychosocial health, for example, the biological indicators may be indicative of one or more dimensions such as stress, depression, activity, time spent outdoors, and/or social interactions.

The system is capable of determining and storing baselines for the various biological markers described herein. Based upon sensor data, user-system interaction (e.g., received user inputs), and/or other external data, the system is capable of comparing the biological markers with the baselines. In an embodiment, the system is capable of continuously collecting sensor data and/or other types of data described herein and performing comparisons between updated states of the biological markers and the baselines. In an embodiment, the baselines for the biological markers may be determined prior to, or at the start, of a rehabilitation program and compared with the state of the biological markers at or near the end of the rehabilitation program.

In many cases, a rehabilitation program may last for a significant period of time such as 8-12 weeks. Typically, a rehabilitation program for a user specifies a variety of specific, well-defined exercises and activities that are to be performed. If the rehabilitation program is followed closely by the patient, the system is able to detect improvements in biological markers compared to baselines of the biological markers. Thus, in one or more embodiments, the system is capable of using the biological markers to determine whether a patient has complied with the rehabilitation program based upon comparisons of the biological markers with the baselines for the biological markers.

In an embodiment, the system is capable of receiving one or more values specified using a visual analog scale (VAS) for one or more of the dimensions described herein. The VAS values, for example, may be specified by a medical professional such as a nurse or a doctor at one or more times throughout the rehabilitation program to assess the progress of the patient in the rehabilitation program. The system is capable of validating the VAS values using the biological marker data that is generated. For example, improvement in a VAS value for exercise training as determined by a medical provider should coincide with an improvement in one or more of the dimensions of exercise training as reflected in the biological markers determined from the sensor data.

Figure 4:
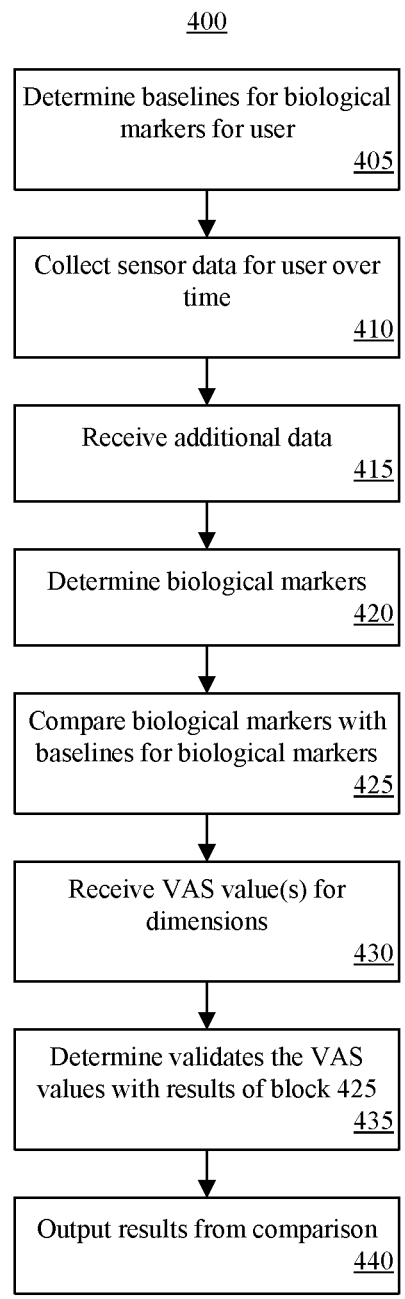
FIG. 4 illustrates an example method of evaluating rehabilitation program compliance.

FIG. 4 illustrates an example method 400 of evaluating rehabilitation program compliance. Method 400 can be performed by a system the same as or similar to the system described in connection with FIG. 1. Method 400 may begin in a state where a patient is prescribed or directed by medical personnel to undergo a particular rehabilitation program.

In block 405, the system determines one or more baselines for biological markers for the patient. In one or more embodiments, the system measures biological markers for the patient over the course of a set time period such as at the start of the rehabilitation program. The patient may wear or keep a device, system, or sensors as described in connection with FIG. 1 on the patient's person throughout the day for that time period, e.g., a week. As such, the system is capable of measuring biological markers throughout the time period as the patient participates in the rehabilitation program. During the time period during which baselines are determined, the patient may be supervised to ensure that particular exercises are performed correctly with the requisite warm-up and/or cool-down periods. The system is capable of generating one or more baselines for the biological markers from the sensor data collected during the initial time period.

The following describes baseline generation for evaluating rehabilitation program compliance by a patient. The sensor data, baselines, and/or biological markers may be stored in databases as described in connection with FIG. 2 or within other data storage devices using any of a variety of data structures.

In an aspect, the system is capable of generating one or more baselines of biological markers indicative of dimensions of exercise training. The biological markers include user activity as determined from accelerometer sensor data and/or target heart rate as determined from heart rate sensor data. The user exercises during the baseline generation time period in a supervised setting as part of the rehabilitation program. The system collects sensor data such as accelerometer data, heart rate data, and the like during that time period. In some cases, e.g., cardiac rehabilitation patients of advanced age that may have musculoskeletal problems such as joint pains and/or other mobility constraints, the warm-up and cool-down are performed in a strict, well-defined manner as opposed to an ad-hoc type of warm-up and/or cool-down thereby facilitating baseline generation and detection of such activities in the future.

The sensor data is correlated with the time and date to generate the baseline biological markers for dimensions of exercise training. Using accelerometer data and the known exercise regimen followed by the patient as part of the rehabilitation program, the warm-up period, cool-down period, exercises, and target heart rate are correlated with the accelerometer data and/or heart rate data to generate baselines of biological markers for each of the noted dimensions of exercise training. Thus, baseline biological markers relating to exercise training, for example, specify accelerometer data, e.g., a signature, for the various exercises performed by the patient, for the warm-up period, and/or for the cool-down period. Since the baseline biological markers are correlated with time, each is capable of indicating the particular time that the patient exercises each day, the length of time the patient exercises each day, and/or the length of warm-up and/or cool-down periods. As noted, baseline biological markers for exercise training may also specify a target heart rate overall or on a per-dimension basis.

In an aspect, the system is capable of generating one or more baseline biological markers indicative of dimensions of self-management. Regarding blood pressure, for example, the system is capable of determining blood pressure, e.g., systolic blood pressure, based upon PPG morphology. The system, for example, is capable of determining systolic blood pressure for a user based upon the area beneath the curve of a PPG waveform. Greater area beneath the PPG waveform coincides with greater systolic blood pressure. Thus, in using the PPG morphology, a blood pressure sensor is not required. The PPG signal data is correlated with time and/or day in order to generate the baseline biological marker indicative of the blood pressure dimension.

Regarding blood glucose, weight management, smoking, and/or fluid intake, for example, the system is capable of receiving data inputs indicating baselines for the various quantities noted. The baselines may be determined by a medical professional.

Regarding sleep, for example, the system is capable of determining quality of sleep for the patient using accelerometer data, heart rate data, etc. The system is capable of determining, for example, the amount of time that the user sleeps, the time periods during which the user is asleep, the quality of sleep, etc. The accelerometer data and/or heart rate data is correlated with time and/or day in order to generate one or more baseline biological markers indicative of the sleep dimension.

In an embodiment, the system is capable of recording a state of mind of the patient prior to sleep as part of the biological baselines indicative of sleep. In an embodiment, the system is capable of querying the patient for a speech input that may be analyzed to determine an emotional state of the user based upon speech analysis as previously described herein.

Regarding medication regimen adherence, for example, the system is capable of providing a user interface through which the system is able to receive user specified data indicating whether the patient is adhering to the medication regimen. The user inputs, for example, may indicate that the user has taken all prescribed medications or has not for a particular day and/or time period (e.g., morning and/or evening).

In an aspect, the system is capable of generating one or more baseline biological markers indicative of dimensions of psychosocial health. Regarding stress management, for example, the system is capable of detecting and/or measuring stress in the user from the sensor data. When under stress, for example, the user's ANS arousal and valence are typically in the second quadrant of the Circumplex Model of Emotions, which can be determined by heart rate and heart rate variability analysis where both trend down at the same time. In one embodiment, the system is capable of using heartrate and heartrate variability to determine whether the user is under stress and/or the amount of stress as a baseline. The biological markers indicative of stress may be correlated with time and/or day and stored as baseline biological markers indicative of the dimension of stress and/or stress management.

Regarding depression and/or depression management, for example, the system is capable of generating one or more biological markers from sensor data that are indicative of depression. In an aspect, these biological markers indicate dimensions such as social interactions and excessive home confinement.

Regarding social interactions, the system is capable of collecting information, with patient permission, from call logs of the system, sounds of the patient's voice including conversations, and the like. Using speech analysis and/or other audio processing techniques, the system is able to detect conversations the patient is having with one or more other individuals in person as opposed to communications via phone or other communication technologies such as video chat, instant messaging, etc. from communication logs of the system. The system is able to detect aspects of conversations, e.g., the patient's voice, such as tone and the patient's role in the conversation as being active or passive based upon analysis of the patient's voice quality and/or speech quality. The system is capable of generating baselines of biological markers that are indicative of social interactions, e.g., the amount of social interaction. For example, the system may determine baselines for amount of time spent in "in-person" conversations, time spent talking on the phone, etc.

Regarding home confinement, the system is capable of analyzing sensor data such as location data to determine whether the patient is home and the amount of time spent at home or indoors. Avoiding excessive home confinement where feasible, including spending time outside the home and, if possible, outdoors with nature, can provide health benefits. This is particularly true in the case of mental health by providing an improved sense of well-being. Accordingly, the system is capable of storing one or more biological markers, e.g., location data, correlated with time and/or day as one or more baseline biological markers indicative of time spent at home (e.g., a measure of home confinement). In an aspect, separate baselines may be established for home confinement and for outdoor exposure.

In block 410, the system is capable of collecting sensor data. The system is capable of collecting sensor data over time such as over the time period during which the patient is following a rehabilitation program. In an embodiment, the system is capable of collecting data continuously. In another embodiment, the system is capable of collecting sensor data at set time intervals such as one minute, two minutes, three minutes, etc., at particular times, and/or in response to particular conditions detected by the system.

In block 415, the system is capable of receiving additional data. The system is capable of receiving user inputs provided via an interface. For example, as discussed, the system is capable of receiving user input specifying adherence to a medication regimen, fluid intake, and so forth. The system is further capable of receiving patient speech for analysis. For other dimensions not directly measurable by sensor data and/or user input, the system is capable of accessing a remote system and/or data storage device to retrieve information such as glucose levels and the like.

In block 420, the system is capable of determining biological makers described in connection with block 405, e.g., updated states of the biological markers. In block 425, the system is capable of comparing the biological markers with the baselines for the biological markers. The system is capable of determining whether the current states of the biological markers exhibit improvement, no change, or deterioration as compared to the corresponding baseline biological markers. As such, based upon the comparison, the system is capable of determining whether the dimensions being measured have improved, deteriorated, or remained the same. The system is capable of performing blocks 420 and/or 425 continuously or at predetermined intervals and/or times. It should be appreciated that the intervals for determining updated states of particular biological markers and/or for comparing particular updated states of biological markers with baselines of the biological markers may vary based upon the particular domain and/or dimension that is analyzed.

The following discussion describes example comparisons that may be performed for block 425. Regarding the blood pressure dimension, for example, the system is capable of comparing baseline PPG signal data with the updated state of the PPG signal data to detect any change in systolic blood pressure of the patient.

In an aspect, the system is capable of comparing the baselines for the various dimensions of exercise training with the updated states of the biological markers to determine whether the prescribed exercise regimen of the rehabilitation program is being performed. For example, the system is capable of determining whether the patient has performed the requisite warm-up period, cool-down period, and the particular exercises of the rehabilitation regimen on the days and/or times and for the durations required by the rehabilitation program.

Further, the system is capable of determining whether the patient has reached a prescribed rehabilitation exertion target in terms of rating of perceived exertion (RPE), heart rate, and length of exercise for the various periods noted. For example, the system determines that patient is non-compliant in response to determining that one or more of the exertion targets are not reached and/or in response to detecting that one or more dimensions of exercise training are not performed (e.g., are not detected for a given day) or not performed for the requisite amount of time.

RPE is a measure of physical activity intensity level. RPE is based upon somatic or psychosomatic sensations related to difficulty of exertion that a user experiences during physical activity which lead to symptoms such as increased heart rate, increased perspiration or breathing rate, increased sweating, muscle fatigue, and so forth. In any event, the RPE is generally considered a subjective measure of exertion on the part of the user at least when received as a user input in response to querying the user. The system is capable of receiving a user input specifying an RPE value.

In an aspect, the time series of PPG signal data used as a blood pressure baseline may exhibit a circadian characteristic since the normal blood pressure of a human being is subject to change based upon different times of the day as well as (a fixed) drug regimen. A significant deviation of the estimated blood pressure while accounting for the confounding variable of ANS arousal, as may be measured using heart rate variability methods, can be indicative of non-compliance with the rehabilitation program.

In an aspect, the system is capable of determining whether the patient is subject to stress and whether the amount of stress varies (e.g., is the same, less, or exceeds) the baseline amount of stress based upon heartrate (e.g., energy) and heartrate variability (e.g., mood) of the user both being low (e.g., below a threshold heartrate and/or a threshold heartrate variability) at the same time and/or remaining low (concurrently) for at least a minimum amount of time. Responsive to determining that the heartrate and heartrate variability both are low for at least the minimum amount of time, for example, the system determines that the user is experiencing stress. For example, in a sympathovagal based measurement, the stress scale may be marked for a user from "Very Relaxed" to "Very Stressed." The instances of a "Very Stressed" determination have very high specificity and sensitivity and can be safely labeled as severe stress instances when such instances last for a notable period of time such as more than 30 seconds.

In another embodiment, the system is capable of determining the patient's capacity to cope with stress (e.g., measuring stress resilience). In an example, the system measures the success of stress management during the rehabilitation program by the stress resilience as indicated by heart rate variability. In an aspect, the system detects extreme stress episodes that lead to LHPA axis activation and weights such episodes higher than other episodes.

In an aspect, the system is capable of comparing baseline biological markers for home confinement with updated states of the biological markers for home confinement. In an embodiment, an ambient light sensor may be used for purposes of determining a patient's exposure, or time spent, outdoors. The system, for example, is capable of determining a level or amount of home confinement and/or outdoor activity of the patient, e.g., based on GPS location data. In one or more embodiments, the system is capable of combining the location data with sensor data from an ambient light sensor of the system. Thus, the system is able to validate outdoor presence of the patient based upon detected ambient light compared with an illumination level that may be obtained from a remote data source (e.g., an Internet service) providing a local weather report. In another example, the system is capable of determining whether other particular activities such as exercise are performed indoors or outdoors.

For other quantities such as blood glucose, patient weight, and fluid intake, further received patient inputs or retrieved data may be compared with the corresponding baselines to determine whether the patient is compliant with the rehabilitation program. In one or more other embodiments, the system is capable of detecting and/or measuring one or more of these dimensions using sensor data. In an embodiment, the system is capable of detecting whether a weight increase for the patient may be attributable to edema, which is not indicative of non-compliance with the rehabilitation program. For example, the system is capable of evaluating daily weight of the patient in the context of increasing or decreasing congestion in heart failure or the presence or absence of edema. For example, in cases where the system detects edema in combination with increase in weight, the system may determine that the increase in weight is due to edema. This provides the patient with encouragement for adherence that may be needed during the time when the patient's body is failing to pump blood properly. An example method for detecting and/or measuring edema in a user and/or patient is provided in connection with FIG. 8 below.

In an embodiment, the system is capable of determining a likelihood that the user is smoking based upon sensor data. Using sensor data, for example, the system is capable of determining that the patient is likely smoking in response to detecting that (1) the patient is outdoors; and (2) exhibits respiratory rhythm disturbances as determined from respiration sensor data; and (3) has momentarily depressed SaO2 count; and (4) detects, from PPG of Carboxyhemoglobin (SpCO) and PPG of Methemoglobin (SpMet), momentary increases in each measure concurrently with detecting elements 1, 2, and 3.

In an embodiment, the system is capable of detecting an increase in fluid intake based upon detecting an increase in the area-under-curve of the PPG signal. This may be particularly true in cases where the detected increase is followed after a short interval by episodes of dyspnea, increased SNS activity, other signs of increasing congestion, and is followed the next day by increasing weight as well as edema.

The system is capable of comparing biological markers relating to quality of sleep, depression, etc., with the baseline biological markers. The system is capable of comparing biological markers relating to social interactions with the baseline biological markers. For example, the system is capable of comparing the number of interactions detected (e.g., phone calls, in-person conversations, etc.), the amount of time spent by the patient interacting, the quality of interactions (the particular persons with whom the patient interacts such as friends, relatives, etc., active vs. passive, voice quality, etc.) with the baselines developed for social interaction.

The foregoing examples are provided for purposes of illustration and not limitation. It should be appreciated that the system is capable of determining current states of the biological markers described herein and comparing such current states of the biological markers with the corresponding or same baseline biological markers. Based upon detected changes in the biological markers relative to the baselines, which are correlated with the previously described dimensions, the system determines whether the patient is complying, or has complied, with the rehabilitation program.

In block 430, the system receives VAS scores for one or more or all of the different dimensions of exercise training, self-care, and/or psychosocial health. The VAS scores are assigned by a medical provider for the patient such as a physician, a nurse, physical therapist, etc. The medical provider assigns the VAS scores based upon experience and clinical acumen. The VAS scores may be received by the system at particular times throughout the rehabilitation program, at the beginning and at the end of the rehabilitation program, etc.

In block 435, the system is capable of validating the VAS scores using the results of block 425. An improvement (e.g., an increase) in VAS scores for a given dimension should be validated by improvement in the biological markers indicative of that dimension. For a given dimension, the system is capable of comparing trends in the VAS scores with trends and/or changes in the biological markers indicative of the dimension. The system is capable determining whether trends in the VAS scores coincide with or match like or same trends in the biological markers for the dimension.

In block 440, the system is capable of outputting results of the validation. For example, the system is capable of indicating whether the VAS scores are corroborated by the biological markers across the different dimensions that are monitored and/or measured.

The example embodiments described within this disclosure establish patient compliance with a prescribed rehabilitation program. Further, the example embodiments aid the medical provider and patient in achieving success by providing visibility of patient performance along the dimensions and domains useful for judging rehabilitation program success. A system as described herein may be used in a home-based rehabilitation program or in a more formal setting such as a hospital. The system promotes health risk reduction (e.g., cardiovascular risk reduction), fosters healthy behaviors and compliance with healthy behaviors, reduces disability, and promotes an active lifestyle for patients.

In one or more embodiments, the system is capable of using one or more of the biological markers described herein that are indicators of one or more or all of the dimensions of HRQOL for purposes of determining improvement in health and/or rehabilitation of the user. For example, the system is capable of using the plurality of dimensions of HRQOL as indicators of improvement in rehabilitation of the user. Improvement in rehabilitation if the user as described using HRQOL may be interpreted by the system as a consequence of participating in the rehabilitation program.

Figures 5, 6:
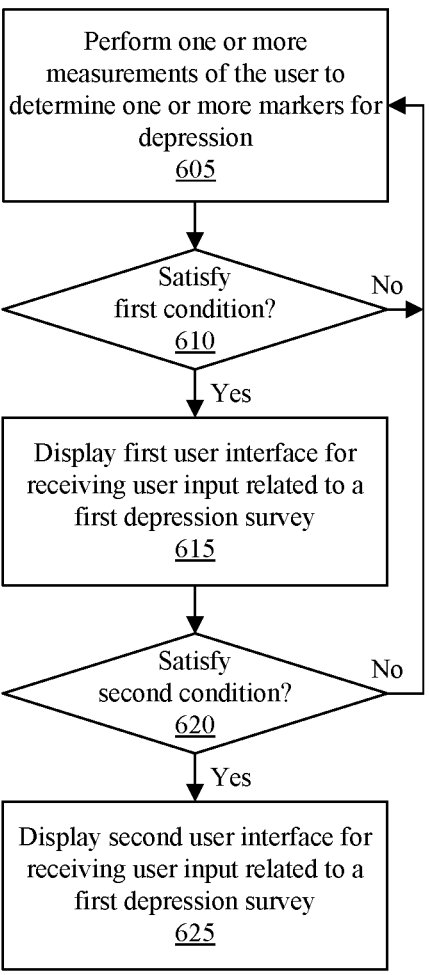
FIG. 5 is an example user interface for presenting a survey.
FIG. 6 is an example method of sensor assisted depression detection.
Figure 7:
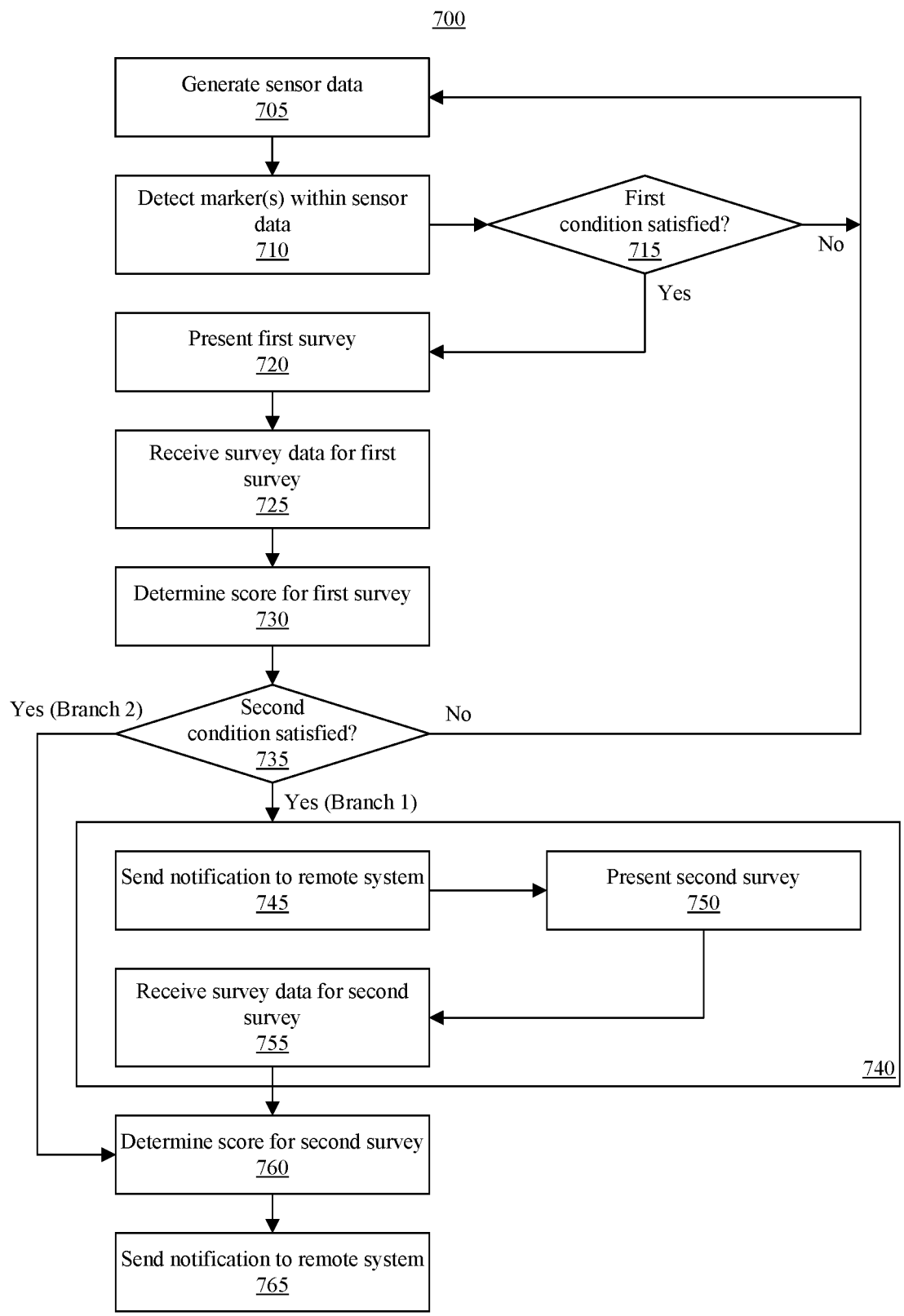
FIG. 7 is another example method of sensor assisted depression detection.

In one or more embodiments, the system is capable of performing an independent depression analysis as described herein in connection with FIGS. 5, 6, and 7. The Patient Health Questionnaire (PHQ)-2 and PHQ-9 are validated screening tools commonly used for depression. Table 1 illustrates the PHQ-2. The PHQ-2 is often used for purposes of screening individuals for depression. The PHQ-2 includes two questions relating to the mood of the user over the past two weeks. The answer given by the user has a score of 0, 1, 2, or 3. The PHQ-2 is scored by summing the score for the two questions.

TABLE 1

| Over the past two weeks, how often have you been bothered by any of the following problems? | Not at all | Several days | More than half the days | Nearly every day |
|---|---|---|---|---|
| 1. Little interest or pleasure in doing things | 0 | 1 | 2 | 3 |
| 2. Feeling down, depressed, or hopeless | 0 | 1 | 2 | 3 |

Table 2 below illustrates the probability of a user having a major depressive disorder or any depressive disorder based upon possible scores of 1, 2, 3, 4, 5, or 6.

TABLE 2

| PHQ-2 Score | Probability of Major Depressive Disorder (%) | Probability of any Depressive Disorder (%) |
|---|---|---|
| 1 | 15.4 | 36.9 |
| 2 | 21.1 | 48.3 |
| 3 | 38.4 | 75.0 |
| 4 | 45.5 | 81.2 |
| 5 | 56.4 | 84.6 |
| 6 | 78.6 | 92.9 |

The PHQ-2 does not have significant resolution for elucidating different aspects of depressive behavior. The PHQ-9 is considered more effective in this regard. Table 3 below illustrates the PHQ-9.

TABLE 3

| Over the past two weeks, how often have you been bothered by any of the following problems? | Not at all | Several days | More than half the days | Nearly every day |
|---|---|---|---|---|
| 1. Little interest or pleasure in doing things | 0 | 1 | 2 | 3 |
| 2. Feeling down, depressed, or hopeless | 0 | 1 | 2 | 3 |
| 3. Trouble falling or staying asleep, or sleeping too much | 0 | 1 | 2 | 3 |
| 4. Feeling tired or having little energy | 0 | 1 | 2 | 3 |
| 5. Poor appetite or overeating | 0 | 1 | 2 | 3 |
| 6. Feeling bad about yourself - or that you are a failure or have let yourself or your family down | 0 | 1 | 2 | 3 |
| 7. Trouble concentrating on things, such as reading the newspaper or watching television | 0 | 1 | 2 | 3 |
| 8. Moving or speaking so slowly that other people could have noticed. Or the opposite - being fidgety or restless that you have been moving around a lot more than usual | 0 | 1 | 2 | 3 |
| 9. Thoughts that you would be better off dead, or of hurting yourself in some way | 0 | 1 | 2 | 3 |

Table 4 below shows how the PHQ-9 is scored.

TABLE 4

| PHQ-9 Score | Depression Measure |
|---|---|
| 1-4 | Minimal depression |
| 5-9 | Mild depression |
| 10-14 | Moderate depression |
| 15-19 | Moderately severe depression |
| 20-27 | Severe depression |

A system, e.g., system 100 of FIG. 1, is capable of collecting data using the various sensors described herein and/or coupled thereto. The system further is capable of analyzing the sensor data to identify or detect one or more markers for depression.

The baselines used for detection of markers of depression may be determined using any of a variety of different techniques. In one embodiment, the baselines may be generalized across a particular population of users. For example, the baselines may have a resolution along an axis of gender, age, socioeconomic conditions, comorbidity, etc. In that case, such baselines are not specific to the user of the system.

In another embodiment, one or more or all of the baselines used may be specific to the user of the system. For example, such baselines may be determined by analyzing the sensor data of the user during times that the user is not experiencing a depressive mood. In a further embodiment, the determination of whether a marker is detected is based upon baselines adapted for evaluation on a daily basis. For example, the baseline may be one that is adjusted for evaluating sensor data for the current day as opposed to evaluating sensor data over a plurality, e.g., 14, days.

The system is capable of selectively administering one or more surveys based upon monitoring a user for one or more of the markers of depression. Within this disclosure, the term "survey" is used interchangeably with the term "questionnaire." In one example, the survey is the PHQ-2 or a derivative thereof. In another example, the survey is the PHQ-9 or a derivative thereof.

The following describes various markers for depression and the detection of such markers. A system as described herein is capable of analyzing sensor data to detect the markers discussed. While the markers described below may be utilized in detecting depression as described in connection with FIGS. 5, 6, and 7, in one or more embodiments, the markers described below may also be used individually or in any combination as biological markers of depression for purposes of evaluating dimensions and/or domains for HRQOL and/or rehabilitation program compliance as described above.

One example marker for depression is a low activity level of the user. The system is capable of determining the activity level of the user using sensor data generated by the accelerometer and/or the motion sensor. The system is capable of comparing the activity level of the user with a baseline activity level. Responsive to determining that the activity level of the user remains below the baseline activity level for at least a minimum amount of time, for example, the system detects the low activity level marker.

In one or more embodiments, the system is capable of classifying activities of the user. The system is capable of performing the classification using accelerometer data and/or location data. The classification may be performed using known machine learning technologies. For example, the system is capable of classifying activities, e.g., daily chores, etc. compared to other more active activities such as exercise. The system is capable of detecting a lack of variety in the activities. For example, the system is capable of detecting that the user performs bare minimum daily chores. The lack of variety in activities is another way of detecting the low activity marker indicating that the user is engaged in a depressive pattern. In one or more other embodiments, the system is capable of using both activity level in combination with activity classification in detecting the low activity level marker.

Another example marker for depression is reduced amount of time spent outdoors (e.g., or too much time indoors). The system is capable of determining whether the user is outdoors (or indoors) from location data generated by the GPS receiver. The system is capable of determining the amount of time that the user is indoors and/or outdoors and comparing the amount of time outdoors with a baseline amount of time. Responsive to determining that the amount of time spent outdoors by the user does not exceed the baseline amount of time, the system detects the marker of spending reduced time outdoors.

Another example marker for depression is being homebound. The system is capable of determining whether the user is homebound (e.g., at home or at a particular location) using location data and comparing the amount of time spend at the designated location to a baseline amount of time. Responsive to determining that the amount of time spent at the designated location exceeds the baseline amount of time, the system detects the homebound marker.

Another example marker for depression is a low level of interaction with other people. Individuals that are depressed tend to spend less time interacting with others and the outside world. Such individuals tend to exhibit an introverted profile, which can significantly reduce the amount of emotional support the individuals may receive at the particular time that emotional support is most needed.

One form of interaction is speaking with other users. In one embodiment, the system is capable of using audio data to determine an amount of time that the user is interacting with other persons. The system is capable of sampling audio using the microphone from time-to-time throughout the day, periodically, or responsive to particular events. For example, the system is capable of sampling audio using the microphone when the user may be engaging in a face to face conversation. The system is capable of analyzing the audio, e.g., performing voice analysis and/or voice recognition, to determine whether the user is speaking and/or speaking with another person. Further, the system is capable of measuring the amount of time spent speaking based upon the analysis. The system further may approximate the amount of time spent speaking based upon the frequency at which samples are acquired and/or the number of samples acquired.

In another embodiment, the system is capable of analyzing call logs, which are considered part of the sensor data for purposes of this disclosure, to determine the amount of time the user spent talking with others. The system is capable of determining the total amount of time using one or both of the techniques described. For example, the system may sum the time spent speaking as determined from the call logs and the sampled audio data.

In one or more other embodiments, the system is capable of determining the amount of time spent, e.g., via call logs, interacting with others through voluntary conversation with friends and/or family members. The party to which the user is speaking and the party's relationship to the user may be determined, for example, from a contact list stored within the system or a contact list that is accessible by the system. The system is capable of using the relationship of the other party on a call as an indicator of the user's level of enthusiasm in interacting with the external world. Lack of enthusiasm is marker of well-known energy dynamics involved in personal interaction with the external world and an indicator of a melancholy mood.

The system is capable of comparing the amount of time spent interacting with other persons with a baseline amount of time for interacting with other persons. The system is further capable of determining a measure of enthusiasm and comparing the level of enthusiasm with an energy dynamics baseline. Responsive to determining that the amount of time spent interacting with other persons does not exceed the baseline amount of time for interacting with other persons and/or that the user's level of enthusiasm is below the energy dynamics baseline, the system detects the low level of interaction marker. In one or more other embodiments, the user's relationship to the other party on a call may be used as a quality factor, e.g., a multiplier, for the call time with that user to weight calls with family or friends more heavily than other calls. Similarly, calls determined to be with persons other than family and/or friends, e.g., business calls and/or telemarketing calls, may be unweighted (have a quality factor of 1) or weighted using a quality factor less than one for purposes of comparison to a baseline. In this manner, calls may be valued differently for purposes of comparison with a baseline based upon the relationship of the party to whom the user is talking.

In another embodiment, the system is capable of analyzing the tone and/or modulation of the user's voice as a marker for depression. The tone and/or modulation of the user's voice is an indicator of mood of the user. The system, for example, is capable of detecting crying, supplicatory speech, apathic (disinterested) syndrome, length in time of pauses, (average) vocal pitch, mean loudness, and/or variation of loudness over time. Responsive to determining one or more of the characteristics of the user's voice noted herein, the system detects a marker of depression. The marker for depression may be an independent marker for depression or a subset of the low level of interaction marker.

Another example marker for depression is decreased sleep. Users with depression may be prone to insomnia or disturbed sleep which can be determined using one or more sensors. For example, the system is capable of measuring sleep of the user using heart rate data and accelerometer data. The system is capable of determining the amount of time that the user sleeps and comparing the amount of time spent sleeping with a baseline amount of time. Responsive to determining that the amount of time the user sleeps does not exceed a baseline amount of time for sleep, the system detects the decreased sleep marker. Another sign of worsening psychophysiological resilience can be detected during sleep via the measurement of heart rate or blood pressure as during sleep a person often has a much lesser extent of dipping phenomenon (for heart rate or blood pressure) as compared to healthy individuals.

Another example marker for depression is significant user supine time. The system is capable of using accelerometer data to determine that the user is supine and the amount of time that the user is supine. The system is capable of comparing the amount of time that the user is supine with a baseline supine time. Responsive to determining that the amount of time that the user is supine exceeds the baseline supine time, the system detects the significant supine time marker.

Another example marker for depression is low ANS arousal. Depression can affect the ANS arousal profile of the user. When under depression the user's ANS arousal and valence are typically in the 3rd quadrant of the Circumplex Model of Emotions, which can be determined by various methods that can detect ANS arousal and valence such as heart rate and heart rate variability analysis where both trend down at the same time. In one embodiment, the system is capable of using heart rate sensor data to determine heart rate and/or heart rate variability. For example, the system is capable of determining whether the user is subject to stress and whether the amount of stress exceeds a baseline amount of stress based upon heart rate (e.g., energy) and heart rate variability (e.g., mood) of the user both being low (e.g., below a threshold for heart rate and/or a threshold for heart rate variability) at the same time and/or remaining low for at least a minimum amount of time.

Another example marker for depression is high stress especially while interacting with the outside world. In one embodiment, the system is capable of using heart rate sensor data to detect stress by determining heart rate and/or heart rate variability. For example, the system is capable of determining whether the user is subject to stress and whether the amount of stress exceeds a baseline amount of stress based upon heart rate (e.g., energy) and heart rate variability (e.g., mood) of the user; with the heart rate being high (above a certain threshold) and heart rate variability being low (e.g., below a threshold) at the same time and remaining so for at least a minimum amount of time. In another embodiment, the heart rate variability method used may be a sympathovagal balance based heart rate variability method. In one or more other embodiments, the system is capable of performing heart rate variability analysis with the external world by sound analysis. In these embodiments, generally the sound is generated from a live source (as in contrast to a sound coming from an electronic media). A user suffering from depression typically has far more instances of stress arousal when interacting with the outside world. The system is capable of comparing the heart rate variability of the user with a baseline heart rate variability given a same or like sound analysis. Responsive to determining that the heart rate variability of the user matches the baseline, the system detects the ANS arousal marker.

In another embodiment, one may use the GSR of the user to detect the arousal level by itself or with the use of heart rate, and use the heart rate variability to detect the valence. In general, any method that can detect that valence and/or arousal can be used to determine if the user is located in the 3rd quadrant of Circumplex Model of Emotions. In cases where the user has limited mobility or where there is a robust EEG method, an EEG based approach can also be used which can provide both valence and arousal. One such EEG sensor is the well-known EEG sensor provided by Emotiv of San Francisco, Calif.

In another embodiment, the system includes one or more sensors, e.g., bio-sensors, configured to determine a heart rate variability profile of the user and an amount of chronic stress episodes experienced by the user, which may activate the LHPA axis. Activation of the LHPA axis may be detected by the one or more sensors.

Other example markers include emotional state, etc. In another embodiment, the system is capable of measuring emotional state using image data obtained from the camera and/or facial recognition sensors. The system is capable of analyzing particular features of the user's facial expression within the image data using, for example, the Facial Action Coding Scale (FACS). The system is capable of detecting those facial features indicative of depressive mood (a depressive emotional state). The system, for example, is capable of comparing features found in images over time to determine the amount of time the user spent in a particular mood. Responsive to detecting one or more such facial features and/or determining that the user is in such a state or mood for at least a minimum amount of time, the system detects the emotional state marker or a particular emotional state.

As discussed, mood recall for a user is often inaccurate. The current mood of the user tends to color or obscure the user's recollection of moods from prior days. In accordance with one or more embodiments described herein, the system is capable of providing questions of the type and/or variety included in the PHQ-2 and/or PHQ-9. The questions may be modified to avoid reference to the past two weeks. For example, the questions may be reformulated to inquire whether the user is currently feeling a particular mood instead of whether the user has experienced such a mood in the past two weeks and how often.

It should be appreciated that to the extent that the markers for depression discussed above also relate to biological markers indicative of particular domains and/or dimensions described in this disclosure, such techniques may be used interchangeably. For example, the call log analysis described herein and other forms of analyzing patient interaction and socialization described herein may be used for purposes of evaluating social interaction dimensions of psychosocial health for rehabilitation program compliance.

FIG. 5 is an example user interface 500 for presenting a survey. The survey provided in user interface 500 is adapted from the PHQ-2 of Table 1. As pictured, rather than asking the user about mood over the past two weeks, the questions presented ask the user about his or her mood at the present time. As such, rather than selecting from one of four different answers that are weighted differently, the user is provided with the binary choice of either "Yes" or "No" in answer to each question.

In one embodiment, the system, responsive to detecting one or more markers for depression, is capable of presenting PHQ-2 type question(s) without reference to the past two weeks. Such a question-set can be regarded as one member of a two week set (e.g., having 14 such instances). Responses of the user may be stored in a database or other data structure which has the above information categorized so that a long term picture can be obtained by linearly adding the responses of the previous 14 days.

At any given time, e.g., during rehabilitation, the system is capable of determining whether the previous 14-days of response(s), e.g., the survey data, exceed a threshold score. In one example, the threshold score may be set to 2 for high sensitivity. In another example, the threshold score may be set to 4 for high specificity. In another embodiment, the threshold score may be determined based upon the available resources and the criticalness of the user's condition. For low resource or relatively less extreme conditions, higher specificity can be targeted. In a setting with relatively abundant monitoring resources or more critical health conditions, a higher sensitivity can be targeted.

In one embodiment, if the score of the user exceeds the threshold score, the system is capable of presenting the PHQ-9 and/or a derivative thereof. Further analysis of the user's state of mind may be performed based upon the PHQ-9. The PHQ-9 can also be administered in the above manner where only a daily "slice" of the PHQ-9 is presented to the user. The information over two weeks is updated and evaluated as is the case for the PHQ-2. In still another embodiment, if the score exceeds a pre-determined threshold, the system may automatically refer the user to a medical provider. In an alternative embodiment, the survey data may be flagged to a medical provider, so that additional investigation can be conducted as to the mental state of the user as appropriate.

Because users are often resistant to filling out surveys and, in particular, surveys directed to depression, the system is capable of automatically administering one or more surveys. The survey(s) may be administered over one or more days, e.g., within a given time interval. The system administers a survey responsive to determining that a condition is met based upon one or more of the detected markers.

FIG. 6 is an example method 600 of sensor assisted depression detection. Method 600 may be implemented by a system the same as or similar to the system described in connection with FIG. 1. In one embodiment, the performance of method 600 may be limited or restricted so that the first survey or the second survey is presented no more than one time per day. Further aspects and details are described below with reference to FIG. 6.

In block 605, the system performs one or more measurements of the user to determine one or more of the markers of depression. For example, the system utilizes the sensors to generate and/or collect sensor data. The system further is capable of analyzing the sensor data to detect or identify markers for depression. In identifying or detecting markers for depression, the system is capable of comparing sensor data that is collected with one or more baselines.

In block 610, the system determines whether a first condition is satisfied. Satisfaction of the first condition triggers presentation of the first survey. In one embodiment, the first condition defines the number markers for depression that are to be detected before a first survey is presented to the user. In one example, the system may satisfy the first condition by detecting one marker during a day. In another example, the system may satisfy the condition by detecting two or more different markers during the day. In any case, if the first condition is satisfied, method 600 proceeds to block 615. If the first condition is not satisfied, method 600 can loop back to block 605.

In block 615, the system displays a first user interface for receiving user input related to a first depressive survey. For example, the system displays one or more questions of the variety of the PHQ-2. As noted, the questions may lack reference to the prior two weeks. For example, the system may present a user interface as described in connection with FIG. 5. The system is capable of receiving survey data in the form of responses to the questions from the user via the presented user interface.

In block 620, the system determines whether a second condition is satisfied. If so, method 600 continues to block 625. If not, method 600 loops back to block 605. In one embodiment, the system determines whether the score of the first survey exceeds a threshold score. The threshold score may be one that is indicative of depression in the user.

In block 625, the system displays a second user interface for receiving user input related to a second depressive survey. In one embodiment, the second survey is the PHQ-9 or a derivative thereof. For example, the questions presented by the second user interface may lack reference to a prior time period as is the case with the first user interface and the first survey.

FIG. 7 is an example method 700 of sensor assisted depression detection. Method 700 may be implemented by a system the same as or similar to the system described in connection with FIG. 1. In one embodiment, the performance of method 700 may be limited or restricted so that the first survey or the second survey is presented no more than one time per day. Further aspects and details are described below with reference to FIG. 7.

In block 705, the system generates sensor data. For example, one or more of the sensors of the system generate sensor data that may be stored in memory of the system as one or more data structures. Examples of sensor data include accelerometer data generated by the accelerometer; location data (e.g., GPS coordinates) generated by the location processor and/or motion sensor; proximity data generated by the proximity sensor; image data generated by the camera subsystem; audio data generated by the audio subsystem; heart rate data generated by the heart rate sensor, and so forth. The system is capable of generating and storing sensor data over a plurality of days.

In block 710, the system is capable of detecting one or more markers within the sensor data. For example, the system is capable of analyzing the sensor data to determine whether one or more markers exist within the sensor data.

In block 715, the system determines whether a first condition is satisfied. Satisfaction of the first condition triggers presentation of the first survey. In one embodiment, the first condition defines the number markers for depression that are to be detected before a first survey is presented to the user. In one example, the system may satisfy the first condition by detecting one marker during a day. In another example, the system may satisfy the condition by detecting two or more different markers during the day. In any case, if the first condition is satisfied, method 700 proceeds to block 720. If the first condition is not satisfied, method 700 can loop back to block 705 to continue generating sensor data and monitoring for marker(s) for depression within the sensor data.

In block 720, the system presents the first survey. The system is capable of presenting the questions of the survey through a user interface of the system. In one embodiment, the system presents the PHQ-2 or an adaptation thereof. As noted, one adaptation is that questions are asked regarding how the user currently feels as opposed to how the user has felt over the past 14 days.

In one example, the system displays the questions of the survey through a visual user interface. For example, the system is capable of displaying a user interface as shown in FIG. 5. While FIG. 5 illustrates both questions being presented concurrently, in another embodiment, the system may present the questions one at a time in serial fashion. In another embodiment, the system may read the questions of the survey aloud to the user. It should be appreciated that the particular modality used to provide the survey through the system is not intended as a limitation of the example embodiments described herein.

In block 725, the system receives survey data for the first survey as specified by one or more received user inputs. The user interface of the system is configured to receive user input providing answers to the questions referred to herein as survey data. The user input may be touch user input, keyboard user input, speech, and so forth. The user input specifying the survey data may be provided using any of a variety of different modalities.

In one embodiment, the system is configured to present the first survey no more than one time within a specific time period. For example, responsive to determining that the first condition is met, the system presents the first survey. The system does not provide the first survey to the user again within the time period regardless of whether the first condition is again met during that same time period. In one example, the time period is a calendar day. In another example, the time period is 24 hours. In order to present the first survey again and obtain further survey data, the system first determines that a new time period has begun and that the first condition is satisfied in the new time period. In one or more other embodiments, however, the system is capable of presenting the survey more than once per time period if a boundary condition is detected. An example of a boundary condition is detecting very high stress for an abnormally long period of time. Such options can be programmed into the system a priori or during the use phase if the care-provider deems it necessary.

The system is further capable of storing received survey data for at least an amount of time necessary to determine a score for the first and/or second surveys. If, for example, the window of time considered for a particular survey is 14 days, the system is capable of storing survey data for at least 14 days. The system may store survey data longer than the required window of time and only utilize the survey data within the window of time when calculating scores for the first and/or second surveys. Appreciably, the system stores the survey data in association with a time and date stamp.

In block 730, the system determines a score for the first survey. In one embodiment, the score is an estimated score. The system determines whether the user provided an affirmative (e.g., a "Yes") answer to each question of the first survey from the survey data. Table 5 below illustrates how each question of the first survey is scored based upon whether the answer was "No" or "Yes." The score for each question is summed to determine a score for the first survey. Within Table 5, the value of N is the number of days that the particular question being scored in the first survey is answered affirmatively over a window of time "M."

TABLE 5

| Answer | Scoring |
| --- | --- |
| No | 0 |
| Yes ($1 \leq N \leq 7$) | $1 + (N - 1)/7$ |
| Yes ($8 \leq N \leq 12$) | $2 + (N - 8)/5$ |
| Yes ($13 \leq N \leq 14$) | 3 |

For purposes of illustration, consider the case where the user is presented with question 1 and answers affirmatively, e.g., with a "Yes." Further, the user has answered question 1 of survey 1 affirmatively one other time within the window of time. The time window is 14 days in this example. In that case, the value of N for question 1 is 2. The system calculates the score for question 1 of survey 1 using the expression $1+(N-1)/7$ with $N=2$ to obtain a score for question 1 of 0.286. The system is capable of storing survey data for the window of time. Thus, with the passing of each day, the window of time is a sliding window of time, e.g., a sliding 14-day window in this example.

The system scores the second question in the same way as question 1. It should be appreciated, however, that the value of N for a question is specific to that question and depends upon the number of times that particular question has been answered affirmatively over the window of time. Since the system scores the question 2 using the same technique as question 1, but using a value of N that is specific to question 2, the particular expression used to determine a score for question 2 may differ from the expression used to calculate the score for question 1.

In further illustration, consider the case where the user is presented with question 2 and answers affirmatively, e.g., with a "Yes." The user has answered question 2 of survey 1 affirmatively 8 other times within the window of time. In that case, the value of N for question 2 is 9. The system calculates the score for question 2 of survey 1 using the expression $2+(N-8)/5$ with $N=9$ to obtain a score for question 2 of 0.6. Again, the system scores the second question using the same technique, where the value of N is determined independently for question 2. As such, in this example, the particular expression used to determine the score for question 2 is different from the expression used to calculate the score for question 1.

In further illustration, consider the case where the user is presented with question 1 and answers affirmatively, e.g., with a "Yes." The user has answered question 1 of survey 1 affirmatively 11 other times within the window of time. In that case, the value of N for question 1 is 12. The system calculates the score for question 1 of survey 1 to be 3. Again, the system scores question 2 using the same technique, where the value of N is determined independently for question 2.

In one embodiment, the window of time or "M" is set to the amount of time or number of days over which the user mood is to be evaluated. For example, both the PHQ-2 and the PHQ-9, when given in a conventional manner, ask the user to evaluate mood over the prior two-week period. The PHQ-2 and/or the PHQ-9 are given one time using a two week look-back period. In the case of FIG. 7, the first survey is given each day that the first condition is met. The score is calculated for that day using the sliding (or rolling) window of time where N is determined for each question independently for the window of time. The window of time is set to 14 days since the look back period for the PHQ-2 and the PHQ-9 is two weeks.

Accordingly, the scoring performed by the system as described with reference to block 730 is adapted for the case where the user answers the survey using binary answers of yes or no with the survey being administered each day that the first condition is met. The PHQ-2 ordinarily utilizes two questions where the user selects one of four possible answers to each question. Each answer is carries a different score. Because the questions of the first survey are directed to how the user is feeling at the time the survey is administered, the responses are binary and the scoring mechanism described above is used.

The expressions described with reference to Table 5 provide a higher bias for higher numbers for N. In another embodiment, a scaling factor nay be added. In still another embodiment, the expressions of Table 5 used may be non-linear for calculating a score for the questions.

In block 735, the system determines whether a second condition is satisfied. If so, method 700 continues down yes branch 1 or yes branch 2. If not, method 700 loops back to block 705 to continue collecting and analyzing sensor data. In one embodiment, the system determines whether the score of the first survey exceeds a threshold score. The threshold score may be one that is indicative of depression in the user.

Yes branch 1 and yes branch 2 illustrate alternative implementations of method 700. Continuing down yes branch 1, for example, the system may perform one or more optional operations illustrated within block 740. In one embodiment, in block 745, the system optionally sends a notification to a remote system. For example, the system may send a message to the system or system of a health care provider, a medical provider, a mental health professional, etc. The message may indicate the score of the first survey or include other data indicating a need for follow-up with the user. The message may be an electronic mail, a text or instant message, an automated call, or another form of communication. The particular type of message that is sent is not intended as a limitation of the embodiments described herein.

In another embodiment, method 700 may bypass block 745 and proceed from block 735 directly to block 750. In block 750, the system may present a second survey. The second survey may be the PHQ-9 or a derivative thereof. In one aspect, the system presents a subset of the questions of the second survey. Within PHQ-9, questions 1 and 2 are identical to questions 1 and 2 of the PHQ-2. Accordingly, since the first two questions of the PHQ-9 are the two questions already presented to the user as the first survey, questions 1 and 2 of the second survey need not be presented.

For example, the system is capable of presenting one or more of questions 3, 4, 5, 6, 7, 8, and/or 9 of PHQ-9. In one embodiment, as noted, the questions are adapted to inquire about the current mood of the user. In one or more other embodiments, the system is capable of estimating answers to a portion of the questions for the second survey based upon sensor data already collected. For example, the system is capable of estimating answers for questions 3, 4, 6, 7, 8, and/or 9 from the sensor data. In illustration, the system may estimate an answer to question 3 based upon accelerometer data and heart rate data or any other suitable sensor or bio-sensing system that is capable of detecting low-valence and low-arousal state of the user's ANS. The system may estimate an answer to question 4 based upon accelerometer data and/or any data that indicates movement or motion of the user. The system may estimate an answer to question 6 using heart rate and/or heart rate variability. In one or more embodiments, the heart rate variability method used may be a sympathovagal balance based heart rate variability or stress determination method. The system may estimate an answer for question 7 based upon activity level of the user. The system may estimate an answer for question 8 based upon audio data, accelerometer data (activity), and/or other motion data such as speed of movement of the user. The system may estimate an answer to question 9 using low valence and low ANS arousal (e.g., as may be indicated by heart rate and/or heart rate variability).

In another embodiment, the system is capable of estimating answers to one or more of questions 3-9 while presenting at least one of questions 3-9 to the user in order to solicit and obtain survey data for the presented question(s). The system is capable of presenting only one or more selected questions of the second survey for which sensor data is less accurate in estimating answers. In one example, the system is capable of presenting only question 5 to the user to obtain survey data for the second survey. In other examples, the system is capable of presenting only questions 5 and 9, presenting only questions 5 and 6, presenting only questions 5, 6, and 9, and so forth.

In block 755, the system receives survey data for each of the questions of the second survey that are presented.

In block 760, the system determines a score for the second survey. As discussed, the system calculates the score based upon any received survey data for the second survey, the score of the first survey (which is the score of the first question and the second question summed), and/or the estimated answers to questions of the second survey as determined from the sensor data. For any questions of the second survey for which an answer is estimated, it should be appreciated that the system is capable of analyzing sensor data over the window of time, e.g., 14 days, to determine a value for N that is question specific and determine a score for the question using the expressions described with reference to Table 5 or derivatives thereof as described herein. Thus, the value of N may be determined for each question of the second survey independently based upon the number of days within the window of time that the markers indicating an affirmative answer to the question are detected. As noted, in some embodiments, in order to detect a marker, the system may need to detect certain characteristics for a minimum amount of time during a day or whatever time period is used as the evaluation period (e.g., 24 hours).

In the case where method 700 proceeds along yes branch 2 from block 735 directly to block 760, the system is capable of estimating an answer for each of questions 3-9 of the second survey. In one embodiment, the system is capable of estimating an answer to question 5 based upon sensor data. In another embodiment, the system may omit question 5 and adjust the scoring for the second survey accordingly. In any case, the system is capable of determining a score, e.g., an estimated score, for the second survey using only the score of the first survey and the estimated answers to the questions of the second survey as determined from the sensor data.

In block 765, the system optionally sends a notification to a remote system. For example, the system may send a message to the system or system of a health care provider, a medical provider, a mental health professional, etc. The message may indicate the score of the second survey or include other data indicating a need for follow-up with the user. The message may be an electronic mail, a text or instant message, an automated call, or another form of communication. The particular type of message that is sent is not intended as a limitation of the embodiments described herein.

In one or more other embodiments, additional sensors may be incorporated to provide measurements that, if available, may be used with the scores. Care providers may be provided information about markers (e.g., for depression or psychological state in general) as computed by the system and/or such other sensors. For example, ECG, camera, and/or ultrasound are several such sensors to determine the RR-intervals and, hence determine if both heart rate and heart rate variability trend downward (indicating that the emotion of the user is in the 3rd quadrant of the well-known Circumplex Model of Emotions, which is where depression is located). In one embodiment, the magnitude of heart rate variability and heart rate changes can be assigned a proportional weight based upon the physiological traits of the given person. For example, an elderly person who is taking beta blockers may not see much elevation in heart rate when under stress but will find the effect on heart rate variability to remain significantly large. Such information can be programmed in the system by the physician who is aware of what marker of ANS is dampened due to medication or an existing pathology. This information can also be programmed using publicly and widely available databases of the FDA approved medicines and their side effect.

In one or more other embodiments, the system is capable of querying the user to measure stress right before sleep and/or measuring the quality of sleep to obtain information about the sleep related portion of PHQ-9, e.g., question 3.

In one or more other embodiments, the system is capable of examining pattern(s) of activities of the user. The system, for example, is capable of detecting a sudden decrease in number of active periods along with a decrease in total activity with concomitant changes in other sensor based markers. The system may use such information to answer vitality related portions of PHQ-9 such as question 4.

In one or more other embodiments, the system may obtain daily weight related measurements. The system is capable of estimating an answer to the portions of PHQ-9 relating to changes in appetite, e.g., question 5.

This disclosure uses the PHQ2 and PHQ9 as example depression screening tools. The examples presented herein, however, are not intended as limitations of the embodiments described. Other depression screening tools may be used in place of the PHQ2 and/or PHQ9. In one or more embodiments, a survey such as the Major Depression Inventory (MDI) may be used as a screening tool. In one or more other embodiments, a survey such as the Web-Based Depression and Anxiety Test (WB-DAT) may be used as a screening tool. In each case, the scoring mechanisms described within this disclosure may be used and/or adapted to such other screening tools. For example, responsive to automatically detecting one or more of the markers for depression described herein, the system is capable of providing one or more of the screening tools (e.g., surveys) to the user.

Figure 8:
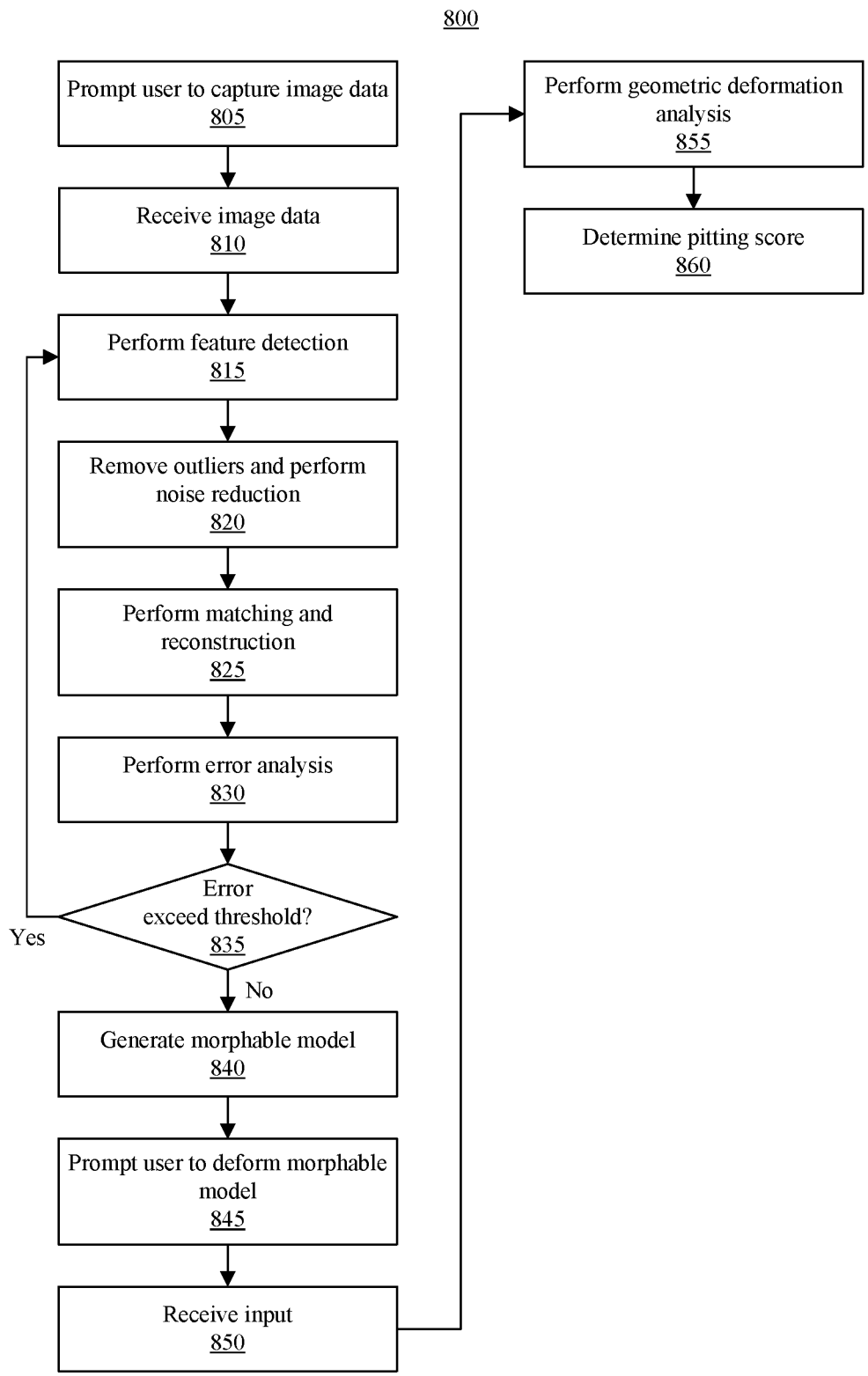
FIG. 8 illustrates an example method of image analysis for edema.

FIG. 8 illustrates an example method 800 of image analysis for edema. Method 800 may be performed by a system the same as or similar to the system described in connection with FIG. 1. In an embodiment, the system provides an option for determination of pitting edema or the dependent edema where questions for potentially more invasive image capture are either prompted by a medical service provider (e.g., a nurse) for determination of either of the cases of edema by the medical service provider (through evaluation of the images as may be provided via a communications link) or are prompted by the system for determination of either of the cases of edema by the system. In either case, the user can be trained before beginning the program as to proper capture of images when the user feels that symptoms associated with edema may be experienced.

FIG. 8 illustrates a general method where the patient is asked to capture image data of a body part of the patient or of the patient's body in general. The image data may be taken from multiple, different viewpoints. The system uses the image data to generate a three dimensional (3D) model of the body part of the patient. In one aspect, the 3D model is converted into a morphable model that allows the system to analyze an amount of pitting in the body part. The morphable model is manipulated through patient intervention (e.g., user inputs) or programmatically (e.g., automatically) to estimate the level of edema suffered by the patient.

Method 800 may begin in block 805, where the system prompts the patient to capture image data. In one or more embodiments, in response to determining that there is a likelihood that the patient is under emotional pressure such as being stressed, fearful, or in pain, the system prompts the patient to capture image data.

The system is capable of prompting the patient to capture image data from multiple, different viewpoints. In one aspect, the system prompts the patient through a patient interface of the system. The prompt can provide instruction as to camera position of the system in relation to the patient. In case of error in image data capture, the system provides feedback to the patient to re-initiate the capture process.

In one or more embodiments, the system is capable of selecting a particular body part for which image data is to be collected. For example, in response to a determination that the patient has a low activity level or has spent a greater amount of time in a supine position (e.g., as compared to an expected amount of time or baseline amount of time spent in the supine position), the system may select the buttocks as a candidate body part for purposes of edema evaluation. The prompt provided from the system indicates the particular body part for which image data is to be collected. As noted, in cases where the patient is inactive, as determined from sensor data, the edema may be dependent. The system may determine that any edema detected is dependent based upon determining that the activity level of the patient is below a threshold and/or detecting that the patient has spent a minimum amount of time in a supine position prior to the edema analysis described herein.

In the case where the system determines that the patient is active and/or has not been in as a supine position as described above, the system selects a different body part such as fingers, arms, and/or legs for purposes of image data collection and edema evaluation.

In block 810, the system receives the image data. The received image data may be labeled in accordance with the particular body part that the patient was asked to capture. For example, an image received in response to prompting the patient for an image of the patient's arm may be labeled "arm" in memory by the processor. Further, as noted, the system may instruct the patient, as part of the prompting, to capture more than one image of the selected part of the body from multiple, different viewpoints.

In response to receiving the image data, the system is capable of processing the image data using one or more computer vision technique(s). In one aspect, the image processing includes multiple stages. The system is capable of analyzing received image data for quality. In an aspect, the system is configured to provide a prompt to indicate that the image is insufficient for purposes of analysis in a variety of different circumstances. In an example, the system is capable performing image analysis to determine whether the image is of a minimum acceptable quality, e.g., having sufficient or a minimum amount of illumination. If not, the system may provide a prompt to the user to retake the image data in the case where the image data is determined to be of insufficient quality for accurate analysis.

In block 815, the system is capable of analyzing the image data using low level computer vision feature analysis. The system is capable of performing feature detection and extracting feature descriptors. Examples of feature that may be detected and/or extracted include, but are not limited to, scale-invariant feature transform (SIFT), histogram of oriented gradients (HOG), and so forth. In block 820, the system is capable of removing outliers from the extracted features. Further, as part of block 820, the system is capable of reducing noise in the extracted features.

In block 825, the system performs matching and reconstruction. In one aspect, within block 825, the system combines the image data, which includes images of the selected part(s) of the body of the patient under analysis for edema from multiple different viewpoints, into a 3D model of the part of the patient's body. Knowing the body part of the patient being modeled and the extracted features, the system is capable of generating the 3D model by combining the image data. It should be appreciated that if an insufficient amount of feature points are found, the system is capable of prompting the patient to take further images of the part of the patient's body under analysis.

In block 830, the system is capable of performing an error analysis. In one aspect, the system performs a least squares error analysis process to estimate the error in the 3D model. Given a reference human body part, for example, the system is able to calculate a reconstruction error. In block 835, the system determines whether the error exceeds a pre-determined error threshold. If the reconstruction error exceeds the pre-determined error threshold, the system is capable of re-initiating the reconstruction process. Accordingly, method 800 loops back to block 815 to continue processing. If the reconstruction error is at or below the pre-determined threshold, the system begins generation of a morphable model. Accordingly, method 800 continues to block 840.

In block 840, the system generates a morphable model. In one aspect, the system converts the 3D model into a point cloud. The system is capable of rendering the morphable model using a pre-determined texture, a wireframe, etc. on the display of the patient's system.

In block 845, the system prompts the patient to deform the morphable model in proportion to the deformation, or pitting, experienced by the patient on the body part under analysis. For example, the system displays the morphable model on the display of the system and prompts the patient to deform the morphable model to replicate or simulate the pitting experienced by the patient in the modeled body part. In block 850, the system receives a patient input. The patient input (e.g., data), which may be a touch-based input to manipulate the displayed morphable model, deforms the morphable model a given amount. The patient-specified data indicates a deformation to the morphable model. The patient, for example, is capable of applying a stress input to the morphable model.

In block 855, the system is capable of determining geometric characteristics for the deformed morphable model. For example, given the amount of deformation to the morphable model, the system is capable of performing a geometric analysis on the morphable model to calculate geometric characteristics of the deformation, e.g., pitting, such as width and/or length, circumference, depth, and so forth. If the computed geometric characteristics are more than established pre-determined threshold(s) for one or more of the determined geometric characteristics, the system determines that the patient is suffering from edema. It should be appreciated that the system is capable of computing more than one pitting deformation by examining more than one location on the user's body. The locations on the user's body examined by the system may be determined based upon input from the healthcare provider for the user or the user's evaluation of the regions where the user (e.g., the patient) feels to have a significant edema.

In block 860, the system is capable of determining a pitting score (PScore) from the geometric characteristics that are generated. The PScore is an estimate of severity of edema suffered by the patient. The system may utilize any of a variety of pitting scores that correlate depth and/or time for the deformation to rebound with a severity of edema being experienced. In one aspect, the system is capable of sending the PScore to a medical service provider or a system of a medical service provider for further analysis.

In one or more embodiments, the system is capable of evaluating edema based upon how quickly the patient's skin recovers or "rebounds" from pitting. For example, the process described with reference to FIG. 8 may be performed for a first iteration to evaluate the size of pitting initially made. The patient may then be instructed to capture further image data periodically or at particular times, e.g., every 10-40 seconds.

In one aspect, the system is capable of performing image analysis to evaluate how quickly the pitting rebounds. Such analysis may be performed periodically based upon the collected image data (e.g., every 10-40 seconds) without having the patient apply a deformation to the morphable model. In another aspect, the system may present the non-deformed morphable model to the patient periodically. The patient may provide an input indicating the amount of pitting currently experienced by the patient to the morphable model. In either case, the system is capable of determining a rate of rebound for the pitting. In this regard, the system is able to calculate a rate of change in the pitting, e.g., a rebound rate, to better evaluate the severity of the edema.

As such, the geometric characteristics, the PScore, and/or the rebound rate are examples of visual characteristics that may be used during the second stage.

The terminology used herein is for the purpose of describing particular embodiments only and is not intended to be limiting. Notwithstanding, several definitions that apply throughout this document now will be presented.

As defined herein, the singular forms "a," "an," and "the" are intended to include the plural forms as well, unless the context clearly indicates otherwise. As defined herein, the terms "at least one," "one or more," and "and/or," are open-ended expressions that are both conjunctive and disjunctive in operation unless explicitly stated otherwise. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B and C together. As defined herein, the term "automatically" means without user intervention.

As defined herein, the term "computer readable storage medium" means a storage medium that contains or stores program code for use by or in connection with an instruction execution system, apparatus, or device. As defined herein, a "computer readable storage medium" is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. Memory elements, as described herein, are examples of a computer readable storage medium. A non-exhaustive list of more specific examples of a computer readable storage medium may include: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, or the like.

As defined herein, the terms "one embodiment," "an embodiment," "one or more embodiments," or similar language mean that a particular feature, structure, or characteristic described in connection with the embodiment is included in at least one embodiment described within this disclosure. Thus, appearances of the phrases "in one embodiment," "in an embodiment," "in one or more embodiments," and similar language throughout this disclosure may, but do not necessarily, all refer to the same embodiment. The terms "embodiment" and "arrangement" are used interchangeably within this disclosure.

As defined herein, the term "output" means storing in physical memory elements, e.g., devices, writing to display or other peripheral output device, sending or transmitting to another system, exporting, or the like.

As defined herein, the term "processor" means at least one hardware circuit configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "real time" means a level of processing responsiveness that a user or system senses as sufficiently immediate for a particular process or determination to be made, or that enables the processor to keep up with some external process. As defined herein, the term "user" means a human being.

The terms first, second, etc. may be used herein to describe various elements. These elements should not be limited by these terms, as these terms are only used to distinguish one element from another unless stated otherwise or the context clearly indicates otherwise.

A computer program product may include a computer readable storage medium (or media) having computer readable program instructions thereon for causing a processor to carry out aspects of the present invention. Within this disclosure, the term "program code" is used interchangeably with the term "computer readable program instructions." Computer readable program instructions described herein may be downloaded to respective computing/processing devices from a computer readable storage medium or to an external computer or external storage device via a network, for example, the Internet, a LAN, a WAN and/or a wireless network. The network may include copper transmission cables, optical transmission fibers, wireless transmission, routers, firewalls, switches, gateway computers and/or edge devices including edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations for the inventive arrangements described herein may be assembler instructions, instruction-set-architecture (ISA) instructions, machine instructions, machine dependent instructions, microcode, firmware instructions, or either source code or object code written in any combination of one or more programming languages, including an object oriented programming language and/or procedural programming languages. Computer readable program instructions may specify state-setting data. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some cases, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, may be implemented by computer readable program instructions, e.g., program code.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In this way, operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the operations specified in the flowchart and/or block diagram block or blocks.

The computer readable program instructions may also be loaded onto a computer, other programmable data processing apparatus, or other device to cause a series of operations to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the inventive arrangements. In this regard, each block in the flowchart or block diagrams may represent a module, segment, or portion of instructions, which comprises one or more executable instructions for implementing the specified operations. In some alternative implementations, the operations noted in the blocks may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

The corresponding structures, materials, acts, and equivalents of all means or step plus function elements that may be found in the claims below are intended to include any structure, material, or act for performing the function in combination with other claimed elements as specifically claimed.

The description of the embodiments provided herein is for purposes of illustration and is not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art to understand the embodiments disclosed herein. Modifications and variations may be apparent to those of ordinary skill in the art without departing from the scope and spirit of the described inventive arrangements. Accordingly, reference should be made to the following claims, rather than to the foregoing disclosure, as indicating the scope of such features and implementations.

What is claimed is:

1. A system, comprising:
   one or more sensors adapted to generate sensor data for a user, wherein the sensor data is generated during a time period corresponding to a rehabilitation program of the user;
   a memory adapted to store the sensor data as a data structure and store a plurality of baselines corresponding to biological markers for the user; and
   a processor, coupled to the sensor and the memory, wherein the processor is configured to initiate executable operations including:

determining one or more biological markers for the user from the sensor data, wherein the one or more biological markers correspond to one or more dimensions of health-related quality of life;

determining a likelihood that the user is experiencing stress based on comparing the one or more biological markers with respective ones of the plurality of baselines corresponding to the one or more biological markers;

in response to detecting the likelihood that the user is experiencing stress, capturing a plurality of images of a selected body part of the user using a camera of the system, wherein the plurality of images are obtained from multiple different viewpoints;

generating a 3D model of the selected body part from the multiple images and converting the 3D model into a point cloud;

rendering the point cloud as a morphable model of the selected body part on a display device of the system;

in response to a prompt to the user to deform the morphable model in proportion to deformation of the selected body part experienced by the user, receiving a user input that deforms the morphable model;

detecting geometric characteristics of the morphable model as deformed and determining a likelihood that the user has edema based on a comparison of the geometric characteristics with pre-determined thresholds for the geometric characteristics; and outputting a notification on an output device of the system, wherein the notification specifies differences determined between the one or more biological markers and the respective baselines, and the likelihood that the user has edema.

2. The system of claim 1, wherein the one or more sensors include a heartrate sensor configured to generate heartrate sensor data, wherein the one or more biological markers include heartrate and heartrate variability.

3. The system of claim 1, wherein the one or more sensors include an accelerometer configured to generate accelerometer sensor data, wherein the processor is configured to initiate executable operations comprising:

monitoring the sensor data in real time to determine, from the accelerometer sensor data, one or more activities of the rehabilitation program performed by the user based on detecting a predetermined signature in the accelerometer sensor data corresponding to the one or more activities; and wherein the one or more activities correspond to at least one of mobility or self-care of the user.

4. The system of claim 3, wherein the processor is configured to initiate executable operations comprising:

determining a location of the user based on location sensor data generated from a location sensor of the system; and wherein the one or more activities are determined using the location of the user determined from location sensor data.

5. The system of claim 1, wherein the likelihood that the user is experiencing stress is determined based upon an analysis of speech of the user.

6. The system of claim 5, wherein the analysis of user speech evaluates at least one of fundamental frequency, vocal perturbation, timbre, intensity, or rate of speech of the user compared to corresponding ones of the plurality of baselines.

7. A method, comprising:

receiving, using a processor, sensor data for a user, wherein the sensor data is generated by one or more sensors during a time period corresponding to a rehabilitation program of the user;

determining, using the processor, one or more biological markers for the user from the sensor data, wherein the one or more biological markers correspond to one or more dimensions of health-related quality of life;

determining a likelihood that the user is experiencing stress based on comparing, using the processor, the one or more biological markers with respective ones of a plurality of baselines corresponding to the one or more biological markers;

in response to detecting the likelihood that the user is experiencing stress, capturing a plurality of images of a selected body part of the user using a camera, wherein the plurality of images are obtained from multiple different viewpoints;

generating a 3D model of the selected body part from the multiple images and converting the 3D model into a point cloud;

rendering the point cloud as a morphable model of the selected body part on a display device;

in response to a prompt to the user to deform the morphable model in proportion to deformation of the selected body part experienced by the user, receiving a user input that deforms the morphable model;

detecting geometric characteristics of the morphable model as deformed and determining a likelihood that the user has edema based on a comparison of the geometric characteristics with pre-determined thresholds for the geometric characteristics; and outputting a notification on an output device, wherein the notification specifies differences determined between the one or more biological markers and the respective baselines, and the likelihood that the user has edema.

8. The method of claim 7, wherein the one or more sensors include a heartrate sensor configured to generate heartrate sensor data, wherein the one or more biological markers include heartrate and heartrate variability.

9. The method of claim 7, wherein the one or more sensors include an accelerometer configured to generate accelerometer sensor data, wherein the method comprises:

monitoring the sensor data in real time to determine, from the accelerometer sensor data, one or more activities of the rehabilitation program performed by the user based on detecting a predetermined signature in the accelerometer sensor data corresponding to the one or more activities; and wherein the one or more activities correspond to self-care of the user.

10. The method of claim 9, comprising:

determining a location of the user based on location sensor data generated from a location sensor; and wherein the one or more activities are determined using the location of the user determined from location sensor data.

11. The method of claim 7, wherein the likelihood that the user is experiencing stress is determined based upon an analysis of speech of the user.

12. The method of claim 11, wherein the analysis of user speech evaluates at least one of fundamental frequency, vocal perturbation, timbre, intensity, or rate of speech of the user compared to corresponding ones of the plurality of baselines.

13. A computer program product comprising a computer readable storage medium having program code stored thereon, the program code executable by a processor to perform operations, comprising:
- receiving sensor data for a user, wherein the sensor data is generated by one or more sensors during a time period corresponding to a rehabilitation program of the user;
- determining one or more biological markers for the user from the sensor data, wherein the one or more biological markers correspond to one or more dimensions of health-related quality of life;
- determining a likelihood that the user is experiencing stress based on comparing the one or more biological markers with respective ones of a plurality of baselines corresponding to the one or more biological markers;
- in response to detecting the likelihood that the user is experiencing stress,
  - capturing a plurality of images of a selected body part of the user using a camera, wherein the plurality of images are obtained from multiple different viewpoints;
  - generating a 3D model of the selected body part from the multiple images and converting the 3D model into a point cloud;
  - rendering the point cloud as a morphable model of the selected body part on a display device;
  - in response to a prompt to the user to deform the morphable model in proportion to deformation of the selected body part experienced by the user, receiving a user input that deforms the morphable model;
  - detecting geometric characteristics of the morphable model as deformed and determining a likelihood that the user has edema based on a comparison of the geometric characteristics with pre-determined thresholds for the geometric characteristics; and
  - outputting a notification on an output device, wherein the notification specifies differences determined between the one or more biological markers and the respective baselines, and the likelihood that the user has edema.

14. The computer program product of claim 13, wherein the one or more sensors include a heartrate sensor configured to generate heartrate sensor data, wherein the one or more biological markers include heartrate and heartrate variability.

15. The computer program product of claim 13, wherein the one or more sensors include an accelerometer configured to generate accelerometer sensor data, wherein the operations include:
- monitoring the sensor data in real time to determine, from the accelerometer sensor data, one or more activities of the rehabilitation program performed by the user based on detecting a predetermined signature in the accelerometer sensor data corresponding to the one or more activities; and
- wherein the one or more activities correspond to self-care of the user.

16. The computer program product of claim 15, wherein the operations include:
- determining a location of the user based on location sensor data generated from a location sensor; and
- wherein the one or more activities are determined using location of the user determined from location sensor data.

17. The computer program product of claim 13, wherein the likelihood that the user is experiencing stress is determined based upon an analysis of speech of the user.

18. The computer program product of claim 17, wherein the analysis of user speech evaluates at least one of fundamental frequency, vocal perturbation, timbre, intensity, or rate of speech of the user compared to corresponding ones of the plurality of baselines.

* * * * *